(12) United States Patent
Ephrat et al.

(10) Patent No.: US 9,230,061 B2
(45) Date of Patent: Jan. 5, 2016

(54) SYSTEM AND METHOD FOR TEXT EXTRACTION AND CONTEXTUAL DECISION SUPPORT

(75) Inventors: Eyal Ephrat, New York, NY (US); Noam Velam, Hod-Hasharon (IL); Dani Cohen, Nataf (IL)

(73) Assignee: MedCPU, Inc., New York, NY (US)

( * ) Notice: Subject to any disclaimer, the term of this patent is extended or adjusted under 35 U.S.C. 154(b) by 0 days.

(21) Appl. No.: 13/586,723

(22) Filed: Aug. 15, 2012

(65) Prior Publication Data

US 2013/0054512 A1    Feb. 28, 2013

Related U.S. Application Data

(60) Provisional application No. 61/523,680, filed on Aug. 15, 2011.

(51) Int. Cl.
G06F 17/30 (2006.01)
G06F 19/00 (2011.01)
G06Q 50/24 (2012.01)
G06F 17/27 (2006.01)

(52) U.S. Cl.
CPC ............ *G06F 19/325* (2013.01); *G06F 17/273* (2013.01); *G06F 17/30663* (2013.01); *G06F 17/30731* (2013.01); *G06F 19/3456* (2013.01); *G06Q 50/24* (2013.01)

(58) Field of Classification Search
USPC ........ 707/769, 802; 703/27; 705/26.1; 704/9; 715/866
See application file for complete search history.

(56) References Cited

U.S. PATENT DOCUMENTS

| | | | |
|---|---|---|---|
| 2003/0083903 A1* | 5/2003 | Myers | 705/2 |
| 2004/0186705 A1* | 9/2004 | Morgan et al. | 704/9 |
| 2006/0020465 A1* | 1/2006 | Cousineau et al. | 704/257 |
| 2007/0033075 A1* | 2/2007 | Hoffman et al. | 705/3 |
| 2009/0172773 A1* | 7/2009 | Moore | 726/1 |
| 2009/0192822 A1* | 7/2009 | Regulapati et al. | 705/3 |
| 2010/0122220 A1* | 5/2010 | Ainsworth et al. | 715/866 |
| 2011/0145297 A1* | 6/2011 | Singh | 707/802 |
| 2011/0246503 A1* | 10/2011 | Bender et al. | 707/769 |
| 2011/0282642 A1* | 11/2011 | Kruger et al. | 703/27 |
| 2012/0022959 A1* | 1/2012 | Yankovich et al. | 705/26.1 |

OTHER PUBLICATIONS

International Search Report and the Written Opinion issued Sep. 13, 2013, in International application No. PCT/US13/55114.

* cited by examiner

*Primary Examiner* — Etienne Leroux
(74) *Attorney, Agent, or Firm* — Jones Day

(57) ABSTRACT

A contextual analysis system that extracts data elements from an unstructured text input; determines whether the extracted data elements are relevant to a predetermined context; and determines, for the extracted elements deemed as relevant, whether the information contained in the relevant data elements complies with a guideline.

21 Claims, 18 Drawing Sheets

Contraindication

Magnesium sulfate is CONTRAINDICATED

Magnesium Sulfate is contraindicated when the patient has Myasthenia Gravis

[ Close ]

Fig. 15E

SYSTEM AND METHOD FOR TEXT EXTRACTION AND CONTEXTUAL DECISION SUPPORT

CROSS REFERENCE TO RELATED APPLICATIONS

This application claims the benefit to U.S. Provisional Patent Application 61/523,680 filed Aug. 15, 2011.

BACKGROUND

1. Field of the Disclosure

The present disclosure relates to a text extraction and contextual decision support system and method, and in particular to analyzing text information from structured and unstructured sources such that a determination of contextual relevancy and appropriate decision support measures may be carried out.

2. Description of Related Art

User interfaces permit entry of structured and unstructured text information. Unstructured text information may be entered directly as free form text (e.g., typing) or as speech-to-text dictation.

Electronic medical records are currently used in the healthcare industry to provide a centralized repository for a patient's entire medical history. These systems may be accessed remotely over a network such that healthcare providers can access a patient's complete record without relying on physical delivery of paper records. Additionally, current electronic medical record systems accept text data input in the form of both structured and unstructured text.

SUMMARY

Aspects of the present disclosure enable extracting unstructured text information, combining the unstructured text with text information stored in structured fields of an application (including graphical user interfaces), and preparing the combination of text information for utilization in several downstream processes. In particular, the extracted text information may be used to perform contextual analysis as an input to various decision support functions, including comparisons with related guidelines.

For example, once text information is acquired and processed such that the structured and unstructured data are in a single data store, this information can be compared to any set of guidelines and/or rules to determine compliance with expectations. These comparisons may then be utilized to provide decision support functions, thereby allowing the system to act upon the acquired text information both systematically and through user interaction (e.g., prompts and alerts). The system may provide decision support through, e.g., a set of prompts or alerts indicating deviations from established guidelines, or by employing a systematic looping feature.

Aspects of the present disclosure are described herein in a medical context, but the described features are certainly not limited to this field. Regarding the medical field context, one aspect of the present invention accesses and analyzes clinically relevant information contained in Electronic Medical Records (EMRs) and other medical reports documented by structured and unstructured data entry. Unstructured data can comprise 50% or more of the total clinically relevant data in the medical field. This information is critically important for proper clinical analysis and producing effective corresponding decision support. Absent further analysis and processing, free text form cannot be used for decision support—including research, analysis, reporting, and quality control features.

In particular, the present disclosure describes a system and method that accurately extracts key concepts from structured and unstructured text input, performs a contextual analysis on the extracted key concepts, and utilizes the contextually analyzed information to perform decision support functions.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIGS. 15A-E illustrate exemplary prompt displays;

DETAILED DESCRIPTION

Figure 1:
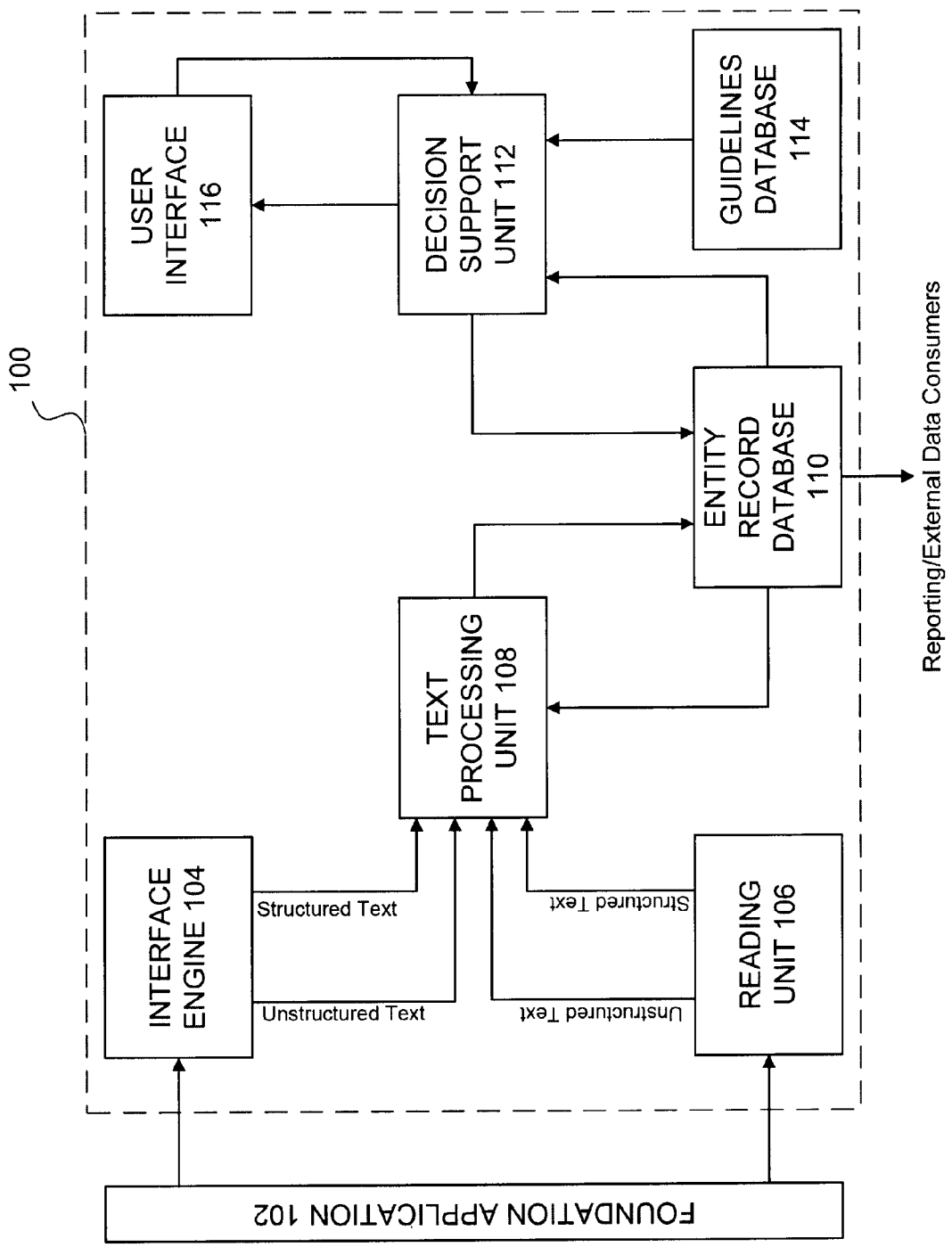
FIG. 1 illustrates a schematic block diagram of an exemplary contextual analysis system.

Referring now to the drawings, wherein like reference numerals designate identical or corresponding parts throughout the several views.

FIG. 1 illustrates a schematic block diagram of an exemplary contextual analysis system 100. As shown in FIG. 1, contextual analysis system 100 may interface with foundation application 102 and include interface engine 104, reading unit 106, text processing unit 108, entity record database 110, decision support unit 112, guidelines database 114, and user interface 116.

Contextual analysis system 100 may receive inputs from an external foundation application 102. Foundation application 102 may be, e.g., dictation transcription software and/or an existing EMR interface installed at a healthcare facility.

Foundation application 102 may output data according to various formats, including the Health Level Seven (HL7) Electronic Health Record standard. Outputs from foundation application 102 may include structured and/or unstructured text information, which is received by interface engine 104 and reading unit 106. In addition, graphical user interface extraction may be supported by the reading unit 106 by, e.g., Microsoft Active Accessibility (MSAA) features.

Text processing unit 108 extracts both unstructured free text data and structured text data from the foundation application 102, as well as data available through other external interfaces (e.g., interface engine 104 and reading unit 106). Text processing unit 108 may extract text information from any source of text data, including unstructured speech-to-text program output. The resultant output of text processing unit 108 is combined text data that is processed such that it is usable to further downstream system features, such as decision support. This output is referred to herein as "harmonized" data.

In the exemplary case of healthcare, text processing unit 108 may extract clinically relevant information from, e.g., hospital patient records, detect and store time-based elements from clinical notes (e.g., "patient began taking prescription medication 'yesterday'"), and/or identify and extract patient conditions.

It should be appreciated that data sourced through unstructured free text or structured data sources cannot be fully relied upon, as the source could contain inaccurate information. Therefore, in the process of harmonizing the structured and unstructured data, text processing unit performs a robust analysis on the incoming data to ensure the quality of all the data in the system repositories. This process includes evaluating the information based on it's context, which may be determined by analyzing incoming and stored information for each respective entity (e.g., patient). In particular, the data may be analyzed by text processing unit 108 by evaluating and comparing the input text data with a set of "truth cases" that are deemed relevant for the particular context (e.g., obstetrics). The evaluation may also include spell correction, tokenization, and tagging. The evaluation performed by text processing unit 108 is preferably done in real-time, but could be applied in batches.

The benefits of acquiring information from multiple sources in both structured and unstructured formats include resolving discrepancies for the partiality of data within each source. Further, combining the relevant and approved matches found in free text with those found in structured data to create a repository of information provides access to most, and potentially all, the data which was previously excluded from analysis (i.e., the unstructured data). In the case of clinical documentation in healthcare, this may result in an upwards of 50% increase in data available for further analysis, including decision support functions.

The foregoing evaluation and comparing process may result in the output of harmonized data, which may include keyword-value pairs. The keyword-value pairs may, e.g., be tagged descriptors and corresponding numerical values indicating a finding, an action, or a problem. It should be appreciated that other elements of contextual analysis system 100 may also generate and perform analysis functions on similar keyword-data pairs. This enables the various elements of contextual analysis system 100 to accurately interpret and systematically review information in the entity record database 110. Guidelines stored in guidelines database 114 may be categorized in this manner as well, thereby enabling the analyzed data to be compared guidelines for decision support. This method also allows for the practice-based guideline acquisition described in later paragraphs, since the process results in usable data wherein, e.g., actions can be tracked, outcomes noted, and lessons learned repositories created.

As an non-limiting illustrative example of the above-described features, text processing unit 108 may evaluate incoming structured and unstructured text information from an EMR interface to determine a patient is 50 years old, experiencing chest pains, has no prior history of heart disease, and will undergo an electrocardiogram (EKG) screening. In this case, text processing unit 108 may output harmonized data including keyword-value pairs of "age=50," "chest pains=Yes," "heart disease=No," and "EKG=Ordered." The harmonized data may also include a time stamp indicating the time and date at which the text information was acquired and processed by text processing unit 108. In this example, keywords are represented to the left of the equality and values are to the right. The values in keyword-value pairs may include, but are not limited to, continuous numerical values, discrete integers, text, or binary values.

Once structured and/or unstructured text information is extracted and processed by text processing unit 108 (i.e., "harmonized"), the harmonized data may be output to entity record database 110. Entity record database 110 is a database storing historical records created around a central entity, which in the medical field is a patient. The entity record database 110 utilizes the combined/harmonized text data and relevant tagging or history of the acquired text data for real-time evaluation and looping processes.

Since the process of collecting data about a particular entity, e.g., a hospital patient, is typically an iterative process with data therefore being collected continuously through time (i.e. whenever a patient interacts with a provider and the EMR is updated), it is important to know what information was available at the time of a particular inquiry. Moreover, clinical decisions in healthcare are made based on newly available information, as well as a patient's medical history. To address these issues, the tagging and time stamping processes of text processing unit 108 and the archiving in entity record database 110 enable the feature of recreating or storing a snapshot view of, e.g., the patient record as of a particular date and time. In particular, the records stored in entity record database 110 may include at least time stamped keyword-value pairs included as part of the text processing unit 108 output. Thus, users of the present invention are provided with an efficient process with which to acquire new information and perform decision support functions based on both the newly acquired and the historical information maintained in the entity record database 110.

It is possible that an entity record stored in entity record database 110 may contain, e.g., an erroneous lab value that might alter a clinical decision (e.g., prescribing medicine to reduce cholesterol based on incorrect low-density lipoprotein (LDL) level). Given the level of scrutiny placed on medical providers and the volume of malpractice suits in the healthcare industry, the quality of historical information stored in entity record database 110 is increasingly important. Further, the usage of Health Information Exchanges (HIE) as information providers will also increase the need for high quality historical information, as healthcare providers are likely to desire a process for saving a particular view of a patient's record, especially when an HIE is a federated model and the data will not be persisted in the HIE itself to provide the record of the patient information at a particular time. Thus, the functions related to extraction and contextual analysis are important to the identification and correction of errors and/or for use in decision support.

Next, entity record database 110 may be configured to store and create an output based on particular criteria for regulatory, compliance, and government use cases. Again, what is unique is that the harmonized data store is created from multiple data sources and from multiple formats (i.e., both structured and unstructured data), which are combined and accessed in various manners, both highlighting the conversion of previously unused unstructured data, as well as the unique capability of combining regulatory guidelines with the data stored in entity record database 110 to provide reports. In the exemplary case of healthcare reporting, contextual analysis system 100 may evaluate data against the requirements and nuances of, e.g., Federal Register reporting guidelines, and enable reporting of this data to external users.

One example of such reporting is the requirement for the healthcare provider to report Body Mass Index (BMI). There are age groups and certain clinical statuses that should not be included in the BMI compliance measure. The elements of contextual analysis system 100 (e.g., decision support unit 112—discussed in detail in later sections) may analyze an EMR stored in entity record database 110 and determine the corresponding patient may be excluded from the BMI reporting requirement, but continue maintaining the BMI data in the patient's EMR. Aspects of this feature are of tremendous value in the marketplace, and this process could be abstracted to any set of predefined requirements for reporting.

As illustrated in FIG. 1, entity record database 110 may also provide an input to text processing unit 108. As discussed in detail in later paragraphs, text processing unit 108 may utilize the historical data contained in entity record database 110 to evaluate against new text information received from interface engine 104 and reading unit 106. This information feedback provides for continuous/recursive contextual analysis of extracted information, which as identified by the present inventor, greatly increases the value of extracted text information at least with respect to automated decision support functions.

In particular, the mere extraction of potentially relevant information without supporting contextual analysis features decreases the processing speed of the system via the inclusion of erroneous data (i.e., higher overall bandwidth is needed), and additionally hinders the user's ability to make effective decisions because of the need to manually evaluate decision support outputs which may otherwise have been eliminated when considering the context of the information. Thus, text processing unit 108 may also be configured to analyze extracted text data to determine relevance to a particular context. The context may be a field or industry (e.g., healthcare, pediatrics), and may also be based on information previously provided (e.g., extracting symptoms and evaluating against the context of medical history, age, sex, etc.)

As a non-limiting illustrative example of this feature, text processing unit 108 may output a keyword-value pair of "Vaginal Bleeding=Yes" after extracting "spotting of red vaginal discharge" in unstructured text input from an EMR speech-to-text input. However, if the patient delivered a child three days prior to this event, automatically recognizing that context greatly assists in performing efficient clinical evaluations because the system can identify that a particular symptom is expected for a given circumstance. Further, by performing contextual evaluation prior to downstream decision support functions, text processing unit 108 eliminates unnecessary information from further processing and precludes, e.g., outputting alerts to the user that provide minimal usefulness and serve only to unnecessarily complicate a decision maker's thought process.

In one aspect, text processing unit 108 may have at least four distinct outcomes from this contextual analysis phase. As described in detail in later paragraphs, these outcomes are recorded in the form of feedback for reevaluation by text processing unit 108, and additionally for future use in historical analysis (i.e., by examining previous records in entity record database 110 when new information is received). The exemplary outcomes include:

Approved: the first outcome is that an extracted keyword-value pair is approved, finding no conflicts or need to modify the output.

Filtered Out: if there is a conflict in the extracted keyword-value pair, it will be discarded and therefore not sent to entity record database 110, effectively eliminating the conflicted data from use in decision support features. For example, if a keyword-value pair of "Preeclampsia=Exist" is extracted while other previously analyzed text input indicates the corresponding patient is not pregnant, the extracted keyword-value pair may be filtered out since it is highly unlikely that a patient that is not pregnant suffers from Preeclampsia.

Modified: text processing unit 108 may find that while an extracted text match could be relevant given other information known about, e.g., a patient from analyzing an existing EMR or previously entered text data, the extracted text match should be modified based on the present context.

Returned: text processing unit 108 may find that while an extracted text match could be relevant given other information known about, e.g., a patient, from analyzing an existing EMR or previously entered text data, the application will create a feedback message resulting in reprocessing of the relevant data.

Create: text processing unit 108 may evaluate an extracted text match based on context and determine a new keyword-value pair should be created to represent a particular context.

The above-described contextual analysis features provide a layer beyond textual extraction and concept matching by enabling additional diligence and processing using industry area of practice criteria before determining if the information discovered in the text data is usable and relevant. Additionally, the efficiency and efficacy of decision support features is greatly improved by contextual analysis relative to other systems providing only text extraction.

Regarding decision support, decision support unit 112 of FIG. 1 enables the coordinated use of the exemplary elements described above to provide decision support features. Decision support may include processing the extracted and contextually analyzed data from text processing unit 108 by actively comparing the data to guidelines and best practice information stored in guidelines database 114 to determine compliance. Based on the comparison, decision support unit 112 may output, e.g., alerts, prompts, triggers, recommendations, reminders, or diagnoses; or provide feedback output to other elements of contextual analysis system 100, such as foundation application 102 (e.g., an EMR interface). Feedback features of decision support unit 112 may be dependent on assigned user roles.

As identified by the inventor, the mere presence of guidelines in guidelines database 114 is insufficient in providing meaningful decision support to the user. Rather, the processing of these guidelines and the preparation and tagging deployed by text processing unit 108 allows for the comparison of the complete set of patient data stored in entity record database 110 against a set of expectations established by the guidelines stored in guideline database 114. Consequently, any gaps between what is stored in the entity record database 110 and what is expected according to the guidelines becomes a source of a trigger, as described in detail in later paragraphs.

There are several sources of guidelines that the decision support unit 112 may access in guidelines database 114. Guidelines sources may be stored locally and/or accessed remotely via a network, such as the Internet. These sources may include:

- Proprietary clinical guidelines developed for use with the system.
- Medical research and key publications, including any research concerning best practices in a medical field.
- Publications from recognized guidelines producing authorities, including any new or modified best-practice guidelines, or recommendations released by recognized authorities in a particular field. Examples of such authorities include the American College of Obstetricians and Gynecologists (ACOG); the Association of Women's Health, Obstetrics and Neonatal Nurses (AWHONN); the Joint Commission on Accreditation of Healthcare Organizations (JCAHO); the Centers for Medicare & Medicaid Services (CMS); the Center for Disease Control (CDC), and the National Institute of Health (NIH).
- Government recommended guidelines (e.g., the Agency for Healthcare Research and Quality (AHRQ)).
- Commercially licensed guidelines (e.g., McKesson Interqual, Milliman Care Guidelines))
- User-identified and harvested best practices. Contextual analysis system 100 provides for ongoing user interaction such that practice protocols identified by the user may be incorporated for use in decision support. Additionally, these user inputs may be "harvested" for incorporation into standardized guidelines sources for wider dissemination.
- Negative outcome root-cause analyses. Root-cause-analysis on each negative outcome case or a significant near-miss may be incorporated for decision support. This analysis is used to identify the root cause for the failure in assuring that the best care possible was provided. This analysis is then applied to determine the corrective measures that should be introduced to guidelines database 114 to assure such failure is mitigated via decision support unit 112 in the future.

It should be appreciated that guidelines sources used by decision support unit 112 are not limited to the medical field. Those of ordinary skill of the art may choose to incorporate guidelines sources corresponding to other fields, as the elements of contextual analysis system 100 may be adapted to extract text information from any source for providing contextual analysis in support of decision support features.

The decision support process performed by decision support unit 112 may provide feedback to the user via, e.g., user interface 116 or foundation application 102. Additionally, decision support unit 112 may provide feedback to other elements of contextual analysis system 100, such as entity record database 110, such that additional and/or recursive looping processing may be performed. The feedback output of decision support unit 112 may include, but is not limited to:

- Triggers: the harmonized data elements of the entity record database 110 are evaluated against the guidelines in guidelines database 114 and a corresponding trigger result is created, based on the evaluation result.
- Prompts: triggers indicating an evaluation result are communicated to users via prompts.
- Roles: prompts are presented to users according to their role.

Any feedback element may be logged and, if desired, output to other monitoring/reporting systems as well.

Next, aspects of the above-described elements of contextual analysis system 100 illustrated in FIG. 1 are described in further detail below, with reference to FIGS. 2-17.

Figure 2:
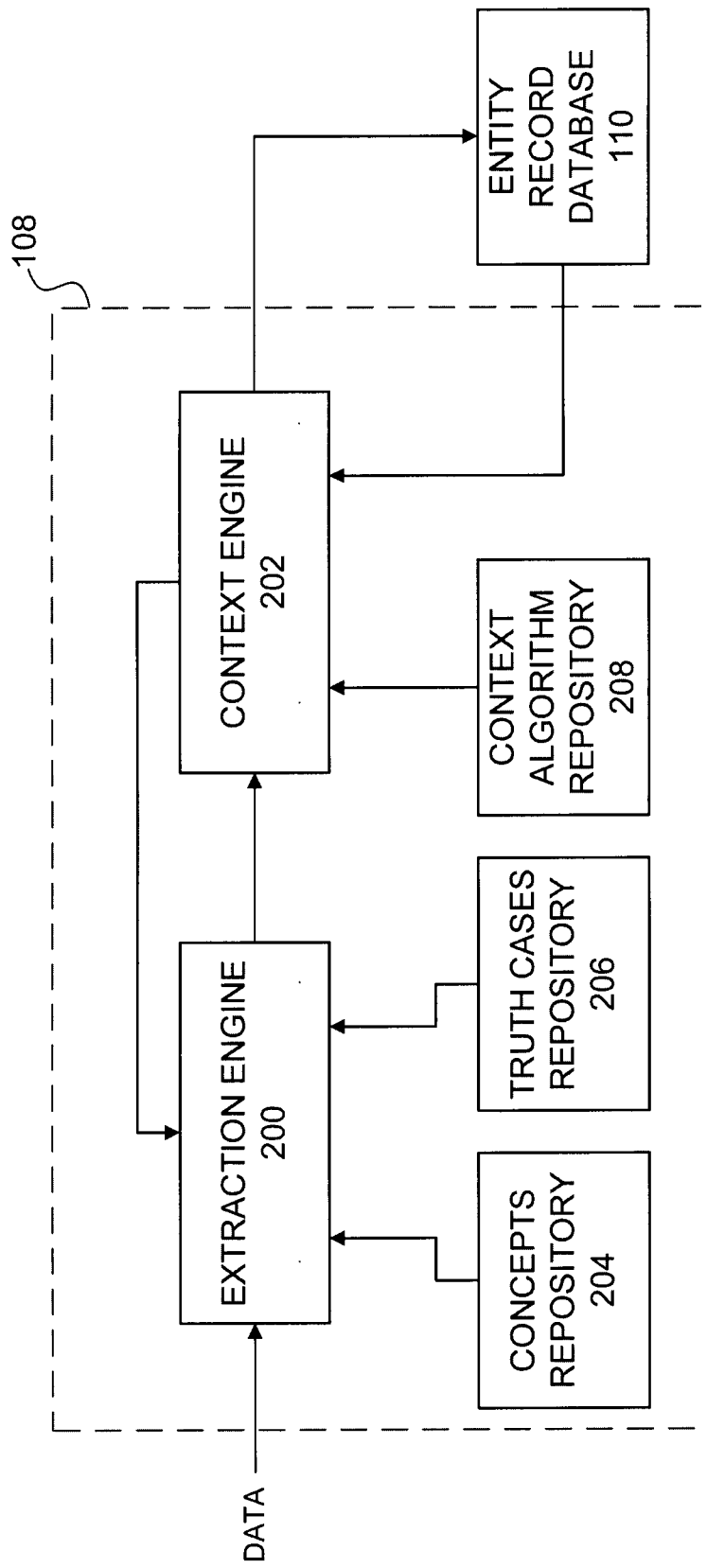
FIG. 2 illustrates a schematic block diagram of an exemplary text processing unit.

An exemplary schematic block diagram of text processing unit 108 is shown in FIG. 2. Referring to FIG. 2, text processing unit 108 may include extraction engine 200, context engine 202, concepts repository 204, truth cases repository 206, and context algorithm repository 208.

The following definitions will be used in describing the features of the text processing unit 108 illustrated in FIG. 2:

- A token is defined as an atomic unit of information (e.g., a word, a number, a punctuation sign, etc.).
- A phrase is defined as a list of tokens (e.g., patient, nkda, child care).
- In a recursive manner, a concept is a container of phrases and other concepts. Concept is a general term that can replace the phrases encapsulated within. For example, the concept "patient" may contain the phrases: patient, pt, pt., he, and she.
- The structure derived from the definition of concepts is defined as a clinical ontology. A concept relates to its parent concept by an "is a" relation (e.g., a "nurse" is a "health provider", a "health provider" is a "person", and a "person" is a word in "English Language").
- Key-concept is defined as a concept of interest outside the text processing unit 108. Key-concepts are expected to have one or more values assigned to them.
- Clusters of key-concepts are sets of key concepts strongly related in a textual sense. For example, a set of key-concepts may be clustered into a group of disease key-concepts.
- Value template is defined as a sign representing mostly (but not only) numerical patterns (e.g., the value template for blood pressure is number_1/number_2). There may be constraints for each element in the pattern and constraints on the relations and order of the elements.
- Header is defined as a tag derived from the text data (e.g., "Assessment and plan:"), from a predefined setting (e.g. "Emergency Room"), from other components of the system (e.g. "Lab results:"), or from context engine 202 (e.g., "Post delivery stage"; see more detailed discussion of context engine 202 features below). A header provides context to extracted data.
- Expression is defined as a textual inquiry (e.g., find all places were the concept "pulse" appears near "blood pressure"). Expressions are a canonical structure of operators, concepts, and value-templates.
- Model is defined as a set of expressions related to a specific key-concept and a specific value or a specific set of values. If the model is true, the key-concept and its values are candidates for extraction.
- Extraction of a key-concept and its assigned values is done by adding them to list of {key-concept, set of values} (also defined as "keyword-value") pairs.

Turning to FIG. 2, the input to extraction engine 200 is unstructured free text data entered from a foundation application or user interface. For example, the input may be dictations entered in an EMR by a clinician (e.g., physician, nurse) during different stages of patient care and documentation. This input may include real-time typed notations, entries using voice-to-text applications, or dictated notes. Extraction engine 200 analyzes and processes the inputted text data and generates a set of key-concepts, each is assigned with one or more values (i.e., a keyword-value pair).

As illustrated in FIG. 2, two repositories support extraction engine 200. First, concept repository 204 contains a highly granular library of concepts that can match specific keywords in the input text data and allow the extraction engine 200 to tag them as candidates for "truth cases" matching. The concepts held in concepts repository 204 may be clinical or general language ontologies, but could also be sourced elsewhere. Concepts repository 204 may store concepts locally and/or access external repositories via a network, such as the Internet.

Second, truth cases repository 206 supports the functionality of the extraction engine 200. It contains a highly granular library of "truth cases" that can match specific set of concepts in the text, as identified by the extraction engine 200.

Functional aspects of extraction engine 200 will now be discussed in detail with reference to FIG. 3.

Figure 3:
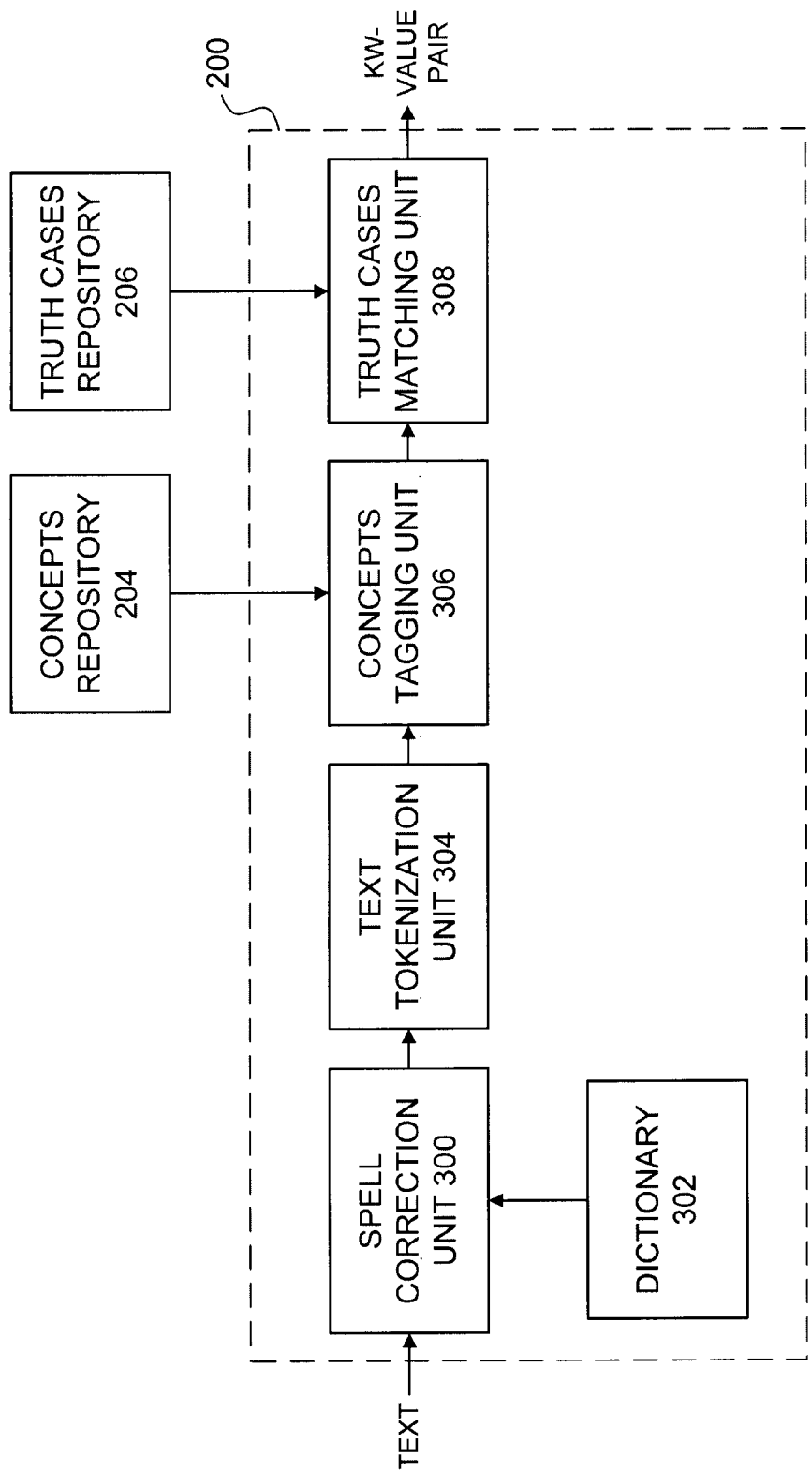
FIG. 3 illustrates a schematic block diagram of an exemplary extraction engine.

FIG. 3 illustrates an exemplary schematic block diagram of the extraction engine 200. Extraction engine 200 receives free text data as input and outputs keyword-value pair candidates to context engine 202. As shown in FIG. 3, extraction engine 200 may include spell correction unit 300, dictionary 302, text tokenization unit 304, concepts tagging unit 306, and truth cases matching unit 308. Spell correction unit 300, concepts tagging unit 306, and truth cases matching unit may respectively, receive inputs from dictionary 302, concepts repository 204, and truth cases repository 206.

Spell correction unit 300 identifies and corrects spelling and grammatical errors of input text data. Because of various reasons, typos and minor spelling mistakes can be abundant in free text data. This issue is especially prevalent in the medical context. While human readers quickly overcome these mistakes, spelling and grammatical errors pose a severe problem in automated text analysis processes, such as those described in the present disclosure. While common spelling correction devices may suggest a list of probable corrections, this practice is not feasible for a system that is intended to operate in the background of another application, such as foundation application 102. In the medical context, the spell correction unit 300 should not correct errors automatically when the probability for accuracy is not high (i.e., close to 100%). Spell correction unit 300 should avoid possible correction errors (i.e., false positives) to the greatest extent possible, as they may lead to inaccurate conclusions by users (e.g., medical staff) and/or decision support elements (e.g., decision support unit 112). If the probability for spell correction unit 300 accuracy is not close to 100%, the preferred response should be to avoid correction altogether (false negative), which allows elements of the contextual analysis system 100 to handle the spelling mistake at a later process (e.g., contextual analysis and subsequent user prompting) while avoiding a false positive correction.

In a non-limiting example, the spell correction unit 300 corrects misspellings where the misspelled word can be transformed to a correct word by:

a. removing/adding a single character (e.g., "patifent" corrected to "patient").

b. replacing a single character (e.g., "cook" corrected to "book").

c. switching two consecutive characters ("thier" corrected to "their").

d. adding/removing doubled letters ("pennicilin" corrected to "penicillin").

e. splitting an incorrect word into two correct words (e.g. "visityesterday" corrected to "visit yesterday").

In a non-limiting example, the spell correction unit 300 uses three tables, which may be stored in dictionary 302:

a. Dictionary: common English words enriched with clinical words (e.g., "hydrocodone"). The criteria by which words are added to the dictionary table is that a word is correct from the standpoint of a user. For example, "pt" (a common medical abbreviation for "patient") is a correct word in the exemplary healthcare context.

b. Exceptions: misspelled words that cannot be corrected effectively by the spell correction unit 300 due to multiple misplaced characters or due to convergence to the wrong correctly spelled word (e.g., "panicelin" corresponding to "penicillin"). The exceptions table is used to bypass the spell correction unit 300 main path correction algorithm and force a specific correction.

c. Characters and their normalized strings (e.g., short dash sign converted to long dash sign). The character normalization table is used by scanning input text data and replacing nonstandard characters with their standard form.

Turning back to FIG. 3, text tokenization unit 304 receives a corrected text input from spell correction unit 300. The corrected text is then tokenized by text tokenization unit 304 using defined Natural Language Processing (NLP) algorithms.

Concepts tagging unit 306 receives unstructured tokenized text input from text tokenization unit 304. As described above, a concept is a list of keywords that belong to the same family. Concepts can carry the same. linguistic or clinical meaning, functionality, role, or category. The features of the concepts tagging unit 306 will be described with reference to the exemplary flowchart of FIG. 4.

For each token received (S400), concepts tagging unit 306 queries the concepts repository 204 for one or more concepts that may correspond to each respective token (S402). Based on the query of concepts repository 204, some concepts in the tokenized text are marked as "triggers" (S404). Triggers are concepts associated with keywords that the concepts tagging unit 306 is seeking to identify and extract from the input text, based on, e.g., the context in which the system is used. For each tagged concept (referred throughout as trigger-concepts), the concepts tagging unit 306 again queries the concepts repository 204 for the concepts marked as triggers (S406). If the concepts tagging unit 306 determines that a trigger is found (S408), concepts tagging unit 306 counts [X] tokens before and after the identified trigger-concept and creates a "triggered block," which is a string of 2[X]+1 tokens, wherein the identified trigger-concept is in the middle of the string (S410). Following the creation of triggered blocks, the output of concepts tagging unit 306 is sent to truth cases matching unit 308.

Figure 4:
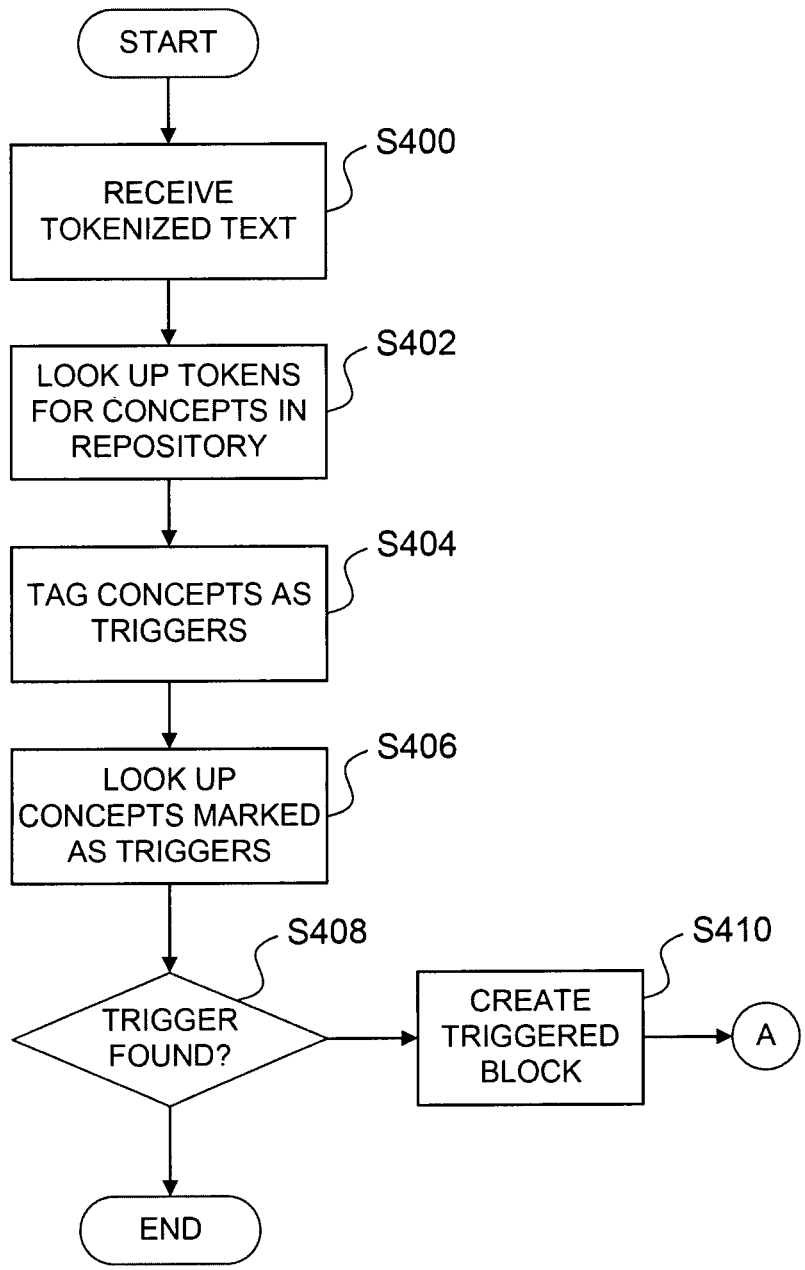
FIG. 4 illustrates an exemplary algorithmic flowchart for an extraction engine.
Figure 5:
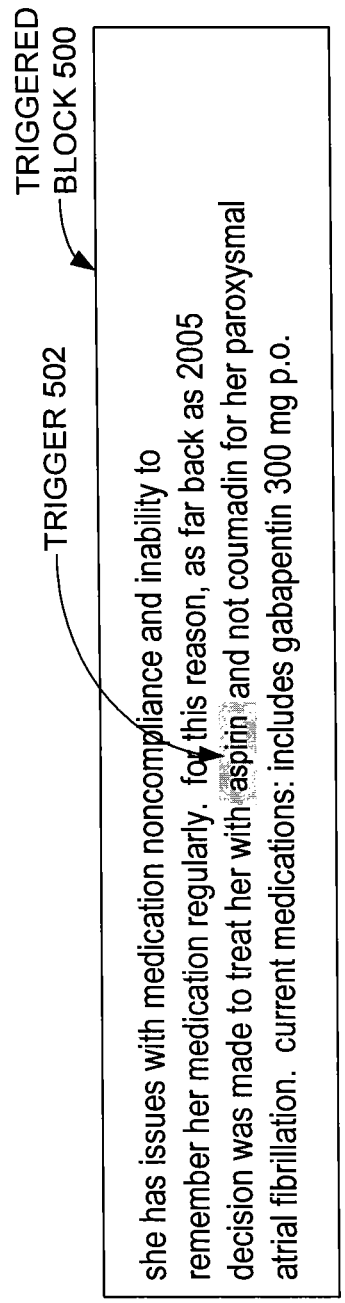
FIG. 5 illustrates an exemplary trigger and triggered block generated by an extraction engine.

For illustration purposes and as a non-limiting example of the process shown in FIG. 4, an exemplary triggered block 500 and trigger 502 are shown in FIG. 5. As discussed above for FIG. 4, concepts tagging unit 306 queries concepts repository 204 for one or more concepts which may correspond to each token. In the example of FIG. 5, concepts tagging unit 306 identifies "aspirin" as a concept to be extracted and tags the term as trigger 502. The concepts tagging unit 306 then identifies the trigger from the input text and creates the triggered block 500, which contains a string of tokens around trigger 502. Triggered block 500 is then output to truth cases matching unit 308.

The conceptualization performed by concepts tagging unit 306 achieves at least four goals. First, noise is reduced in the incoming text data such that only the concepts deemed important are visible/available for further processing. Next, conceptualization results in all synonyms being represented by a single concept, thereby increasing processing efficiency. Next, having the concepts in a hierarchical structure enables using fewer rules addressing high-level concepts that are also value for many of the descendant concepts. Lastly, each concept and value-template contains a set of ranges indicating where it appears in the text, which results in the foundation of the Range-Based Language used by expressions.

Regarding Range-Based Language (RBL), expressions are textual inquiries constructed as RBL operators and operands. The operands include concepts, value-templates, numeric values, and the operators themselves. RBL has three key principles. First, it uses "sets of ranges" as inputs and outputs to the RBL operators, as well as for representations of concepts and value templates. Next, RBL operators can be used in a canonical manner (i.e., the output of an operator can serve as part of the input of another operator). Lastly, RBL supports the reusability of a single rule to cluster key concepts.

Referring back to FIG. 3, truth cases matching unit 308 receives the triggered block output from the above-described process performed by concepts tagging unit 306. Truth cases matching unit 303 also interfaces with truth cases repository 206. A truth case is defined for the purposes of the present disclosure as a set of concepts in a particular order. In general, truth cases matching unit 308 matches reference truth cases stored truth cases repository 206 with sequences of trigger-concepts contained in the input triggered block.

Features relating to truth cases matching unit 308 in a programming phase will now be discussed in detail with reference to FIGS. 6-11.

In general, and as a non-limiting example, truth cases are generated from the triggered blocks by analyzing the concepts included in the triggered block and/or the order in which the concepts appear. Further, truth cases matching unit 308 can generate truth cases regardless of the number of tokens appearing between concepts within a triggered block. The generation in the programming phase is typically bound by a sentence, but truth cases matching unit 308 may also evaluate for truth case generation using any preceding information contained in a header.

Figure 11:
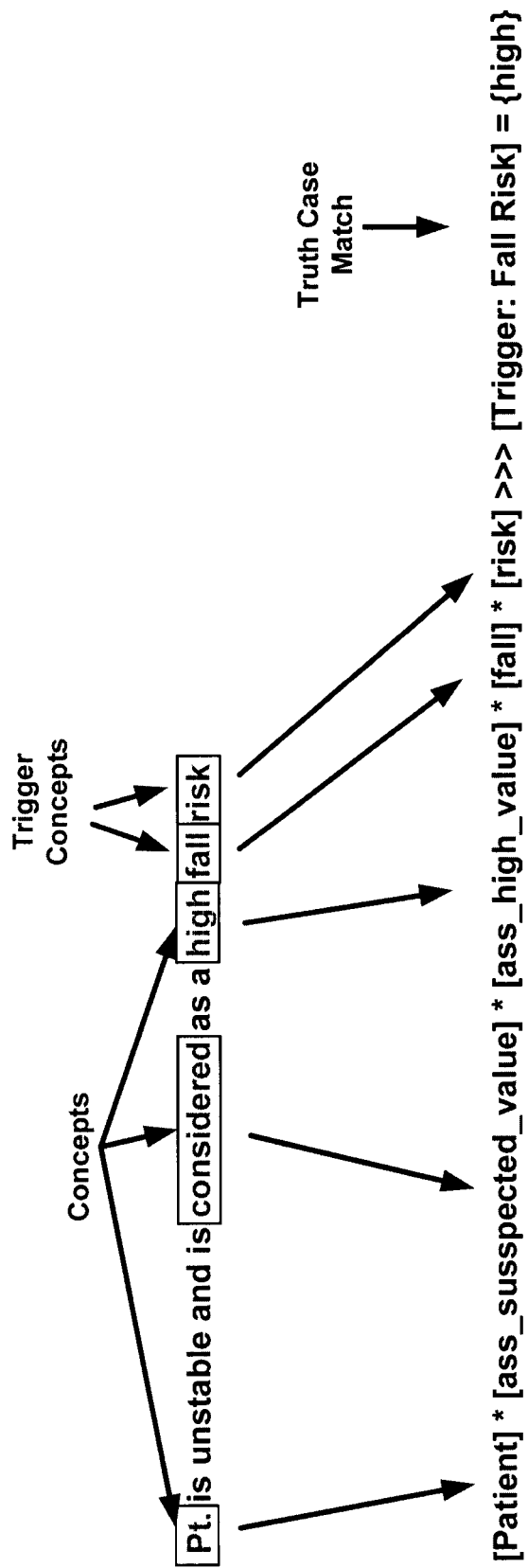
FIG. 11 illustrates an exemplary truth case generation.

For illustration purposes, FIG. 11 provides and example of a truth case generation using an exemplary triggered block, "Pt. is unstable and is considered as a high fall risk." In this example, five concepts were identified by truth cases matching unit 308 (i.e., "Pt.," "considered," "high," "fall," and "risk"). Of these five concepts, "fall" and "risk" were identified as trigger-concepts. The arrows stemming from each identified concept in FIG. 11 point to the parent concept in which the identification is contained. For example, "Pt." is part of the "Patient" concept. In this example, the two trigger concepts result in a trigger of "Fall Risk" being identified for a truth case match. Truth cases matching unit 308 evaluates both the identified concepts and the order in which they occur in the triggered block to determine a value of "high" should be assigned. Thus, a truth case match keyword-value pair of "[Trigger: Fall Risk]={high}" is generated and output to truth cases repository 206.

The creation of truth cases in the programming phase is very valuable with respect to improving the contextual analysis and decision support features of contextual analysis system 100. In particular, the ability to generate accurate and informative truth cases enables improved matching of truth cases when performing the downstream functions.

Figure 6:
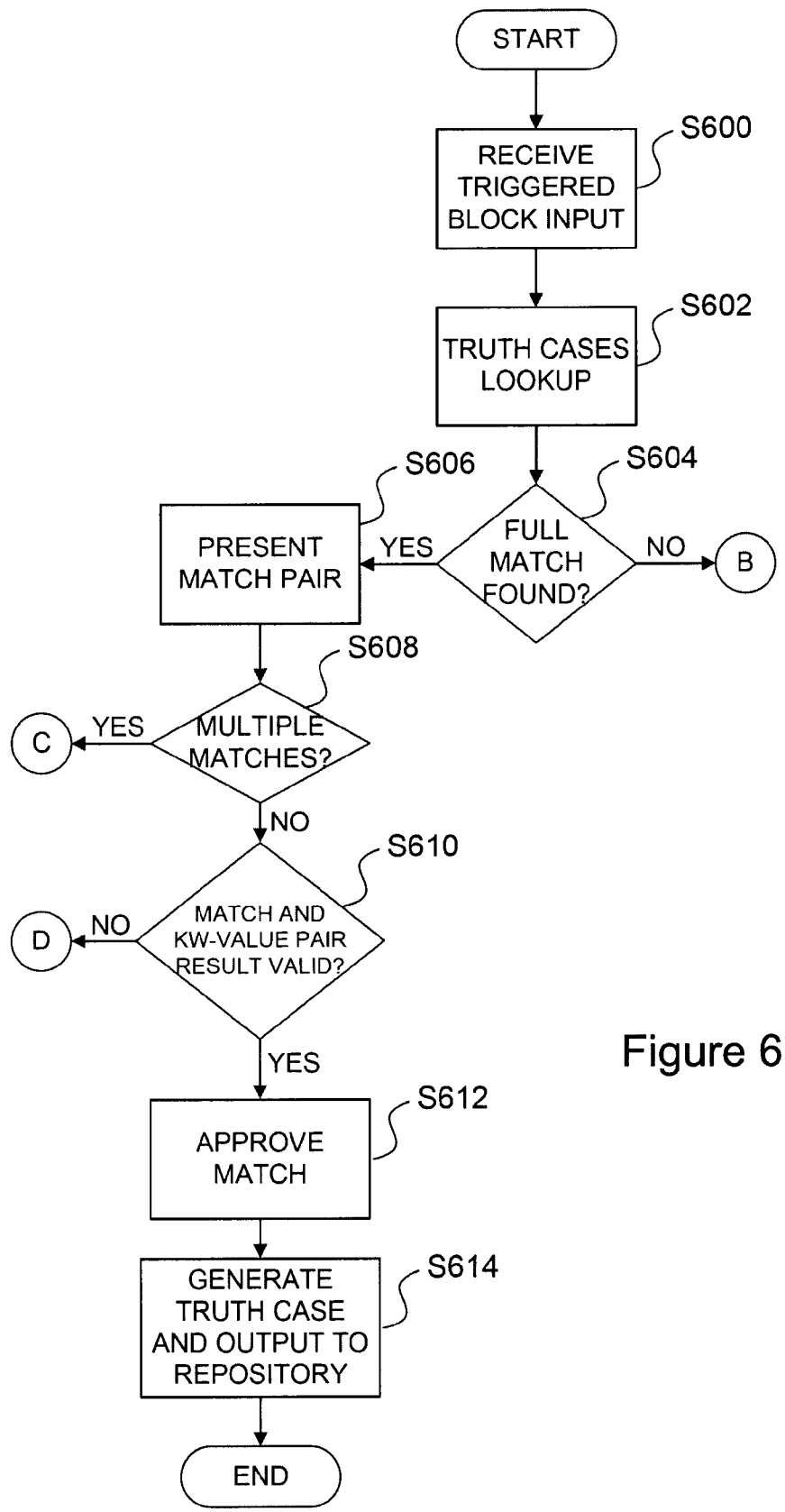
FIG. 6 illustrates an exemplary algorithmic flowchart for a truth case matching unit in a programming phase.

Next, FIG. 6 illustrates an exemplary algorithmic flowchart for the truth cases matching unit 308 in a programming phase. In the programming phase, the truth cases matching unit 308 receives triggered block input from concepts tagging unit 306 (S600). The input data is then searched for a full match between the tagged trigger-concepts in the trigger block input and one of the reference truth cases in truth cases repository 206 (S602). If a full match is not found (S604), then truth cases matching unit 308 performs a "true match" creation function, which will be described in detail with reference to FIG. 7.

Figure 7:
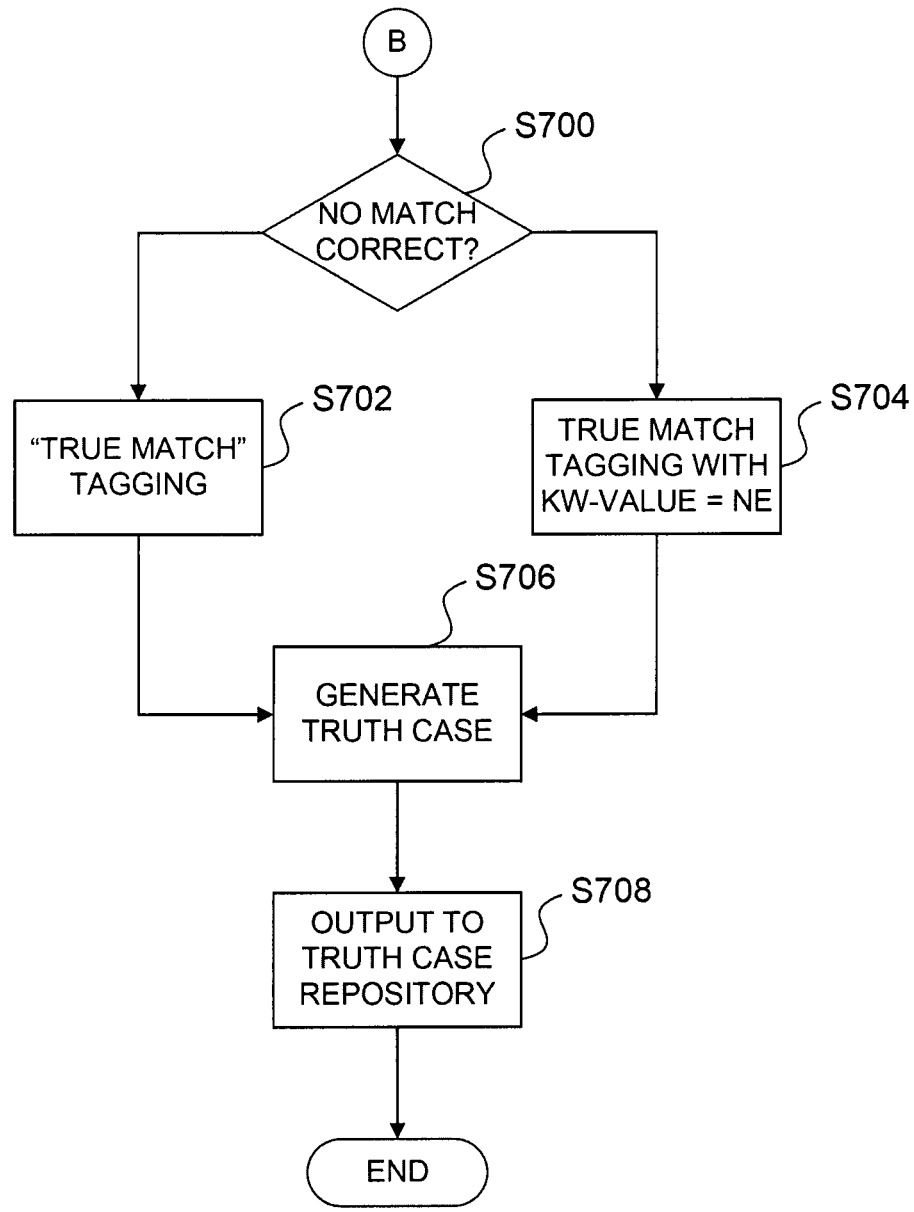
FIG. 7 illustrates an exemplary algorithmic flowchart for a "true match" creation function of a truth case matching unit in a programming phase.

Referring to FIG. 7, after determining a full match is not present in truth cases repository 206, truth cases matching unit 308 determines whether a match should have been made (S700). If a match should have been made and was not, truth cases matching unit 308 identifies and tags the correct trigger-concept sequence in the triggered block input and assigns it to the correct keyword-value pair (S702). If at S700 the truth cases matching unit 308 determines a correct match should not have been found, the truth cases matching unit 308 identifies and tags the correct trigger-concepts sequence in the triggered block input and assigns it to the correct keyword-value pair=No Extraction (NE) (S704). A "No Extraction" value is assigned in instances where truth cases matching unit 308 should not extract a specific keyword-value pair in order to avoid false positives. In both cases, a truth case is generated (S706) and output to truth cases repository 206 (S708).

Returning back to FIG. 6, if a full truth case match is found at S604, the truth case match and associated keyword-value pair is then presented for further analysis (S606). First, truth cases repository 206 determines whether multiple matches were found (S608). If multiple matches are found, then a "true match" resolution process is performed, which will be described in greater detail with reference to FIGS. 8 and 10.

Figure 8:
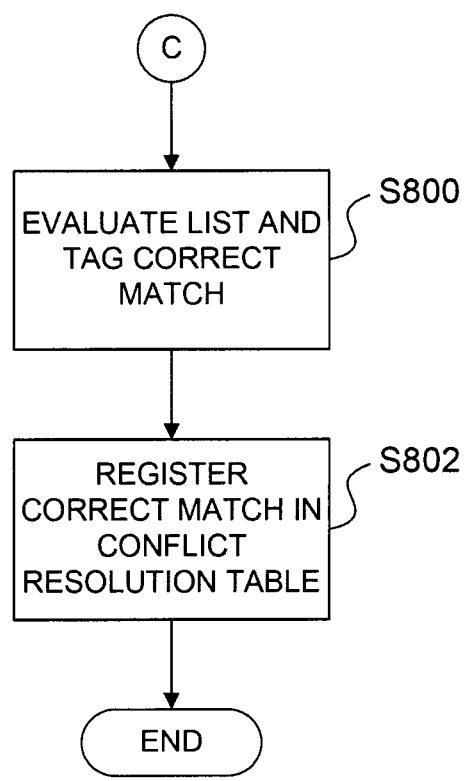
FIG. 8 illustrates an exemplary algorithmic flowchart for a "true match" resolution function of a truth case matching unit in a programming phase.
Figure 10:
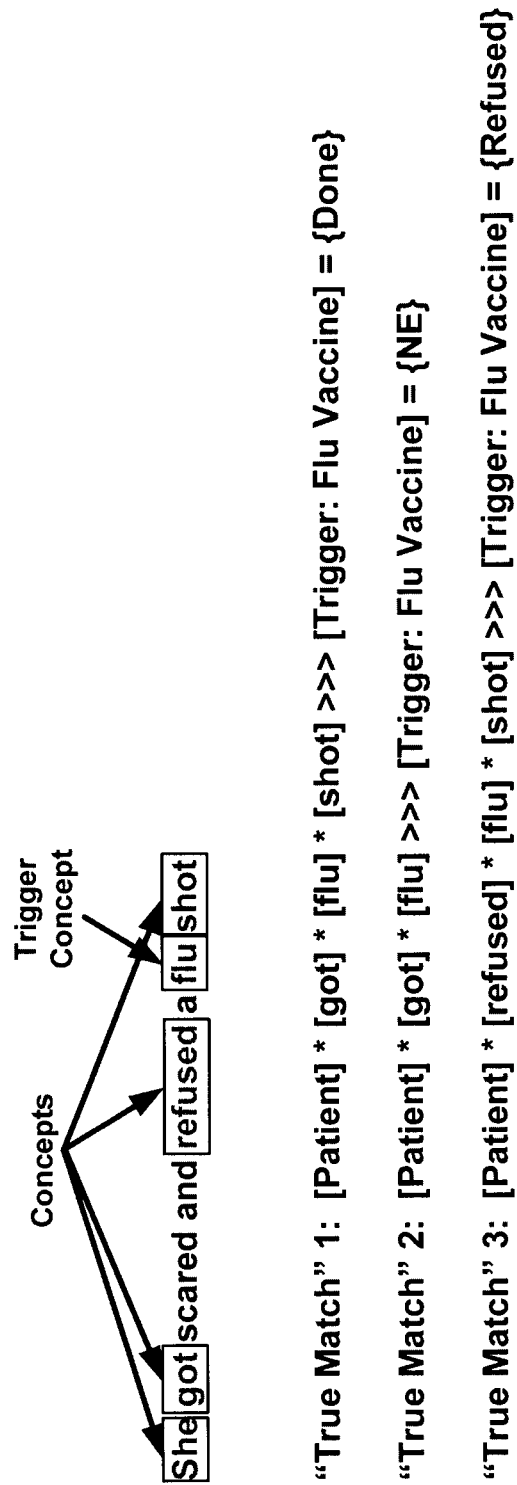
FIG. 10 illustrates an exemplary "true match" resolution.

FIG. 8 illustrates an exemplary algorithmic flow chart for a true match resolution process executed by truth cases matching unit 308. As shown in FIG. 10, multiple matches may be found within a single triggered block input. The example of FIG. 10 shows three true matches resultant from a single trigger block containing the trigger concept "flu." Based upon the other identified concepts in the triggered block and an evaluation of the list of true matches (i.e., S800 of FIG. 8), truth cases matching unit 308 may determine that "True Match 3", shown in FIG. 10, is the correct match. When a correct match is determined, the correct trigger-concepts sequence and its associated keyword-value pair are registered in a conflict resolution table as a winning match over the other possible matches in the corresponding resolution. Thus, truth cases matching unit 308 is able to accurately identify a single match when presented with similar inputs at a later time.

Referring back to FIG. 6, if multiple matches are not found at S608, truth cases matching unit 308 determines whether the single keyword-value (KW-Value) pair result is valid (S610). If not, a "true match" correction process is performed, which will be described in greater detail with reference to FIG. 9.

Figure 9:
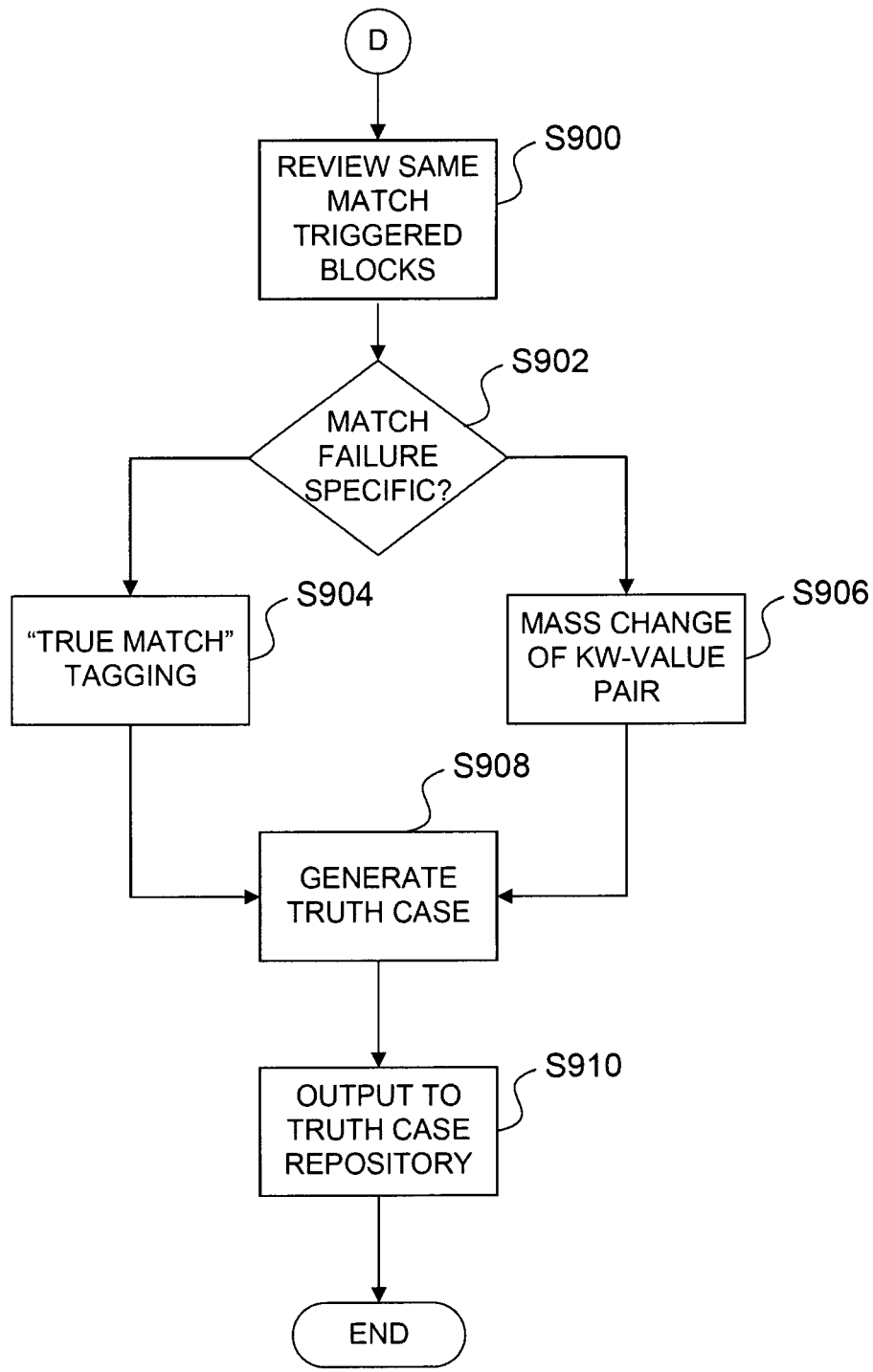
FIG. 9 illustrates an exemplary algorithmic flowchart for a "true match" correction function of a truth case matching unit in a programming phase.

Referring to FIG. 9, truth cases matching unit 308 first evaluates a list of all triggered blocks that generate the same true match with the same keyword value pair and determines whether the current failure to match is specific to the current triggered block, or if a general error in the true match occurred that affects all the triggered blocks for the corresponding true match (S900 and S902). If the match failure is specific to the current triggered block, truth cases matching unit 308 tags the correct trigger-concepts sequence in the triggered block and assigns the correct keyword value pair (S904). Otherwise, truth cases matching unit 308 changes, as a mass change, the keyword value pair for the evaluated true match that will affect all the matched triggered blocks (S906). In both cases, a truth case is generated and output to truth cases repository 206 (S908 and S910).

Referring back to FIG. 6, if truth cases matching unit 308 determines the match and keyword-value pair result is correct at S610, truth cases matching unit 308 approves the match (S612). Once the match is approved, a truth case is generated and output to truth cases repository 206 (S614).

The programming phase of generating and storing truth cases by truth cases matching unit 308 is described above. However, the process of evaluating triggered block input against reference cases to find matches and outputting associated keyword-value pairs to context engine 202 for contextual analysis occurs in a "runtime phase." Features related to truth cases matching unit 308 in the runtime phase will now be discussed in detail with reference to FIG. 12.

Figure 12:
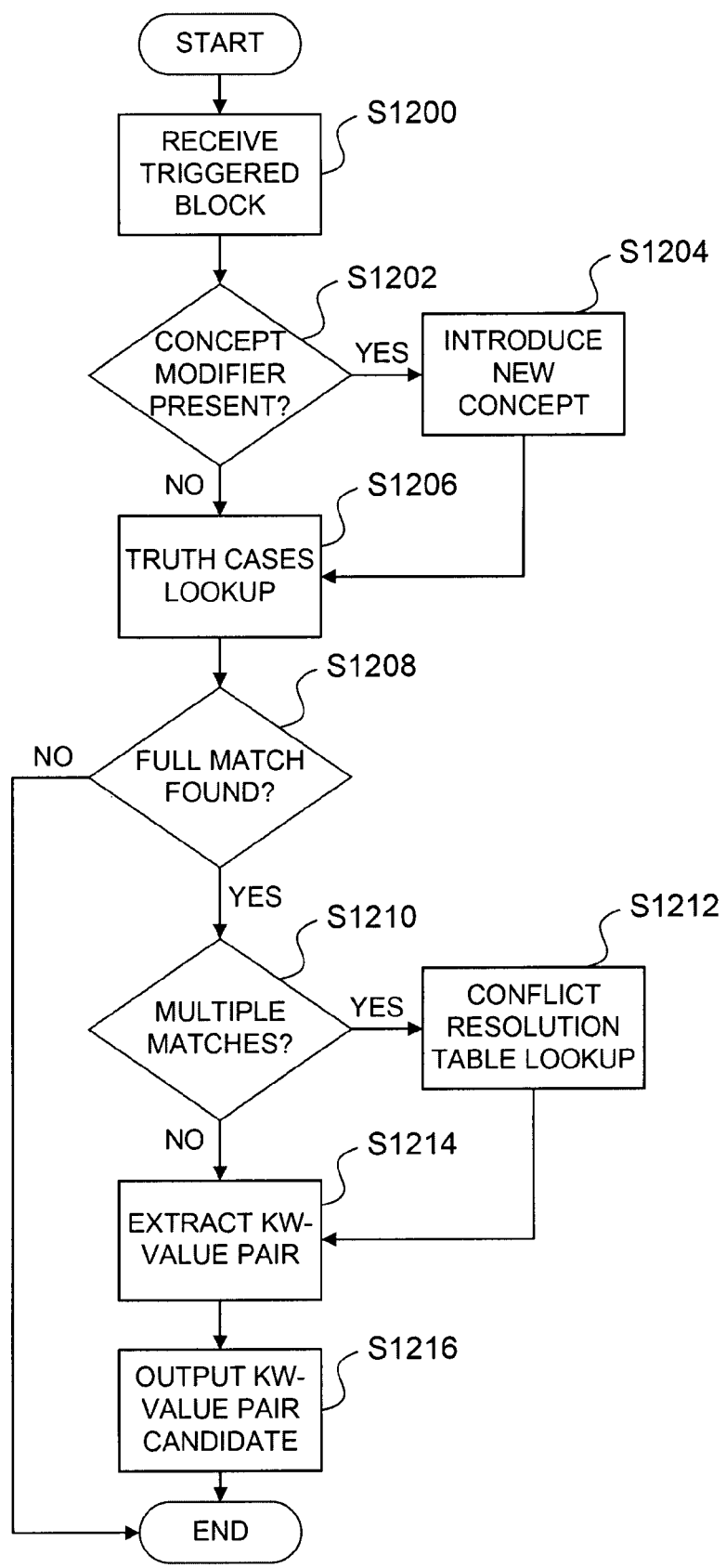
FIG. 12 illustrates an exemplary algorithmic flowchart for a truth case matching unit in a runtime phase.

FIG. 12 illustrates an exemplary algorithmic flow chart for truth cases matching unit 308 in the runtime phase. In the runtime phase, truth cases matching unit 308 receives a triggered block input from concepts tagging unit 306 (S1200). Next, truth cases matching unit 308 determines whether a concept modifier is received from context engine 202 (S1202). If a concept modifier is received (e.g., from the "Returned" case described above for text processing unit 108's contextual analysis features), truth cases matching unit 308 either tags a particular token with the concept modifier in the triggered block or replaces an existing concept in the triggered block with a concept modified by the received concept modifier (S1204). If a concept modifier is not received, the concepts in the input triggered block remains unchanged. In either case, the triggered block is searched for a full match between the sequence of trigger-concepts in the triggered block and at least one of the reference truth cases stored in truth cases repository 206 (S1206). If a full match is found, truth cases matching unit 308 determines whether multiple matches were found (S1210). If so, conflicts are resolved using the conflicts resolution table described for the programming phase above (S1212). In resolving conflicts, truth cases matching unit 308 may, e.g., determine which of the multiple matches is the closest match, based on using statistical tests combined with additional rules and/or a predefined set of priorities used to decide if the conflict may be resolve, and if so, how. Next, a keyword-value pair is extracted from the identified single or resolved best match of the multiple matches (S1214). The extracted keyword-value pair is then output as a keyword-value pair candidate to context engine 202 (S1216).

The aforementioned exemplary processes performed by truth cases matching unit results in extraction engine 200 outputting a keyword-value pair candidate to context engine 202. While the text extraction process performed on structured and/or unstructured text data by extraction engine 200 results in an output which is valuable and usable by other downstream functions, the addition of the features provided by context engine 202 results in valuable synergy benefits that are not obtainable via text extraction or contextual evaluation individually.

Referring back to FIG. 2, text processing unit 108 includes context engine 202, which evaluates each newly created keyword-value pair candidate output from extraction engine 200 against the data (e.g., other keyword-value pairs) stored in entity record database 110. This allows context engine 202 to weigh the contextual significance of the newly created keyword-value pair candidate and analyze it from a particular contextual perspective (e.g., medical).

Figure 13:
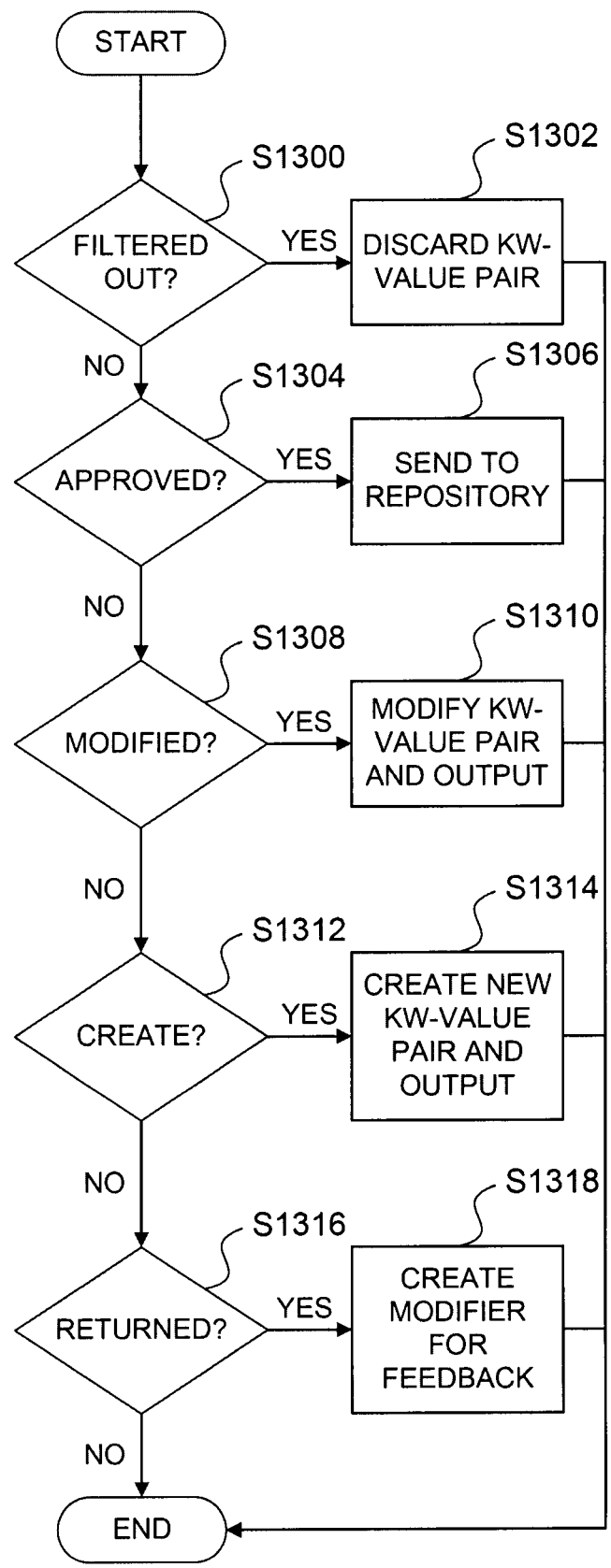
FIG. 13 illustrates an exemplary algorithmic flowchart for a context engine.

As discussed previously, there are several optional results of this evaluation, which are illustrated in the exemplary flow chart of FIG. 13. First, context engine 202 may deem the extracted keyword-value pair candidate irrelevant based on context (i.e., S1300; the "Filtered Out" case discussed previously with respect to text processing unit 108). In this case, no further action is performed and nothing is output to entity record database 110 (S1302).

Next, context engine 202 may deem the extracted keyword-value pair candidate to be relevant and/or accurate based on context (i.e., S1304; the "Approved" case discussed previously with respect to text processing unit 108). In this case, no change or manipulation is performed on the keyword-value pair and it is output to entity record database 110 (S1306).

Next, context engine 202 may deem the extracted keyword-value pair candidate to be relevant and/or accurate based on context, but in need of modification to be consistent with the context (i.e., S1308; the "Modified" case discussed previously with respect to text processing unit 108). For example, the context engine 202 may determine the value in the keyword-value pair candidate may need to be changed to another value. In this case, a new/modified keyword-value pair is created and sent to entity record database 110 (S1310).

Next, context engine 202 may evaluate the extracted keyword-value pair candidate based on context and determine a new keyword-value pair should be created to represent a particular context (i.e., S1312; the "Create" case discussed previously with respect to text processing unit 108). In this case, the new keyword-value pair is output to entity record database 110 (S1314).

Lastly, context engine 202 may determine that a new parameter/modifier should be created and sent back to the extraction engine 200 (i.e., S1316; the "Returned" case described above). In this case context engine 202 may determine, based on contextual analysis, the extracted keyword-value pair candidate received from extraction engine 200 is incorrect, but that there is a possibility that another keyword-value pair could be extracted from the corresponding text if another concept-like parameter would have existed in the triggered block. Such a concept-like parameter might generate a different truth case match that may yield a different keyword-value pair candidate when re-analyzed by extraction engine 200. In this case, the rules governing the context engine 202 operation may generate such a new concept-like parameter and output it as feedback to the extraction engine 200 (S1318).

Figure 14:
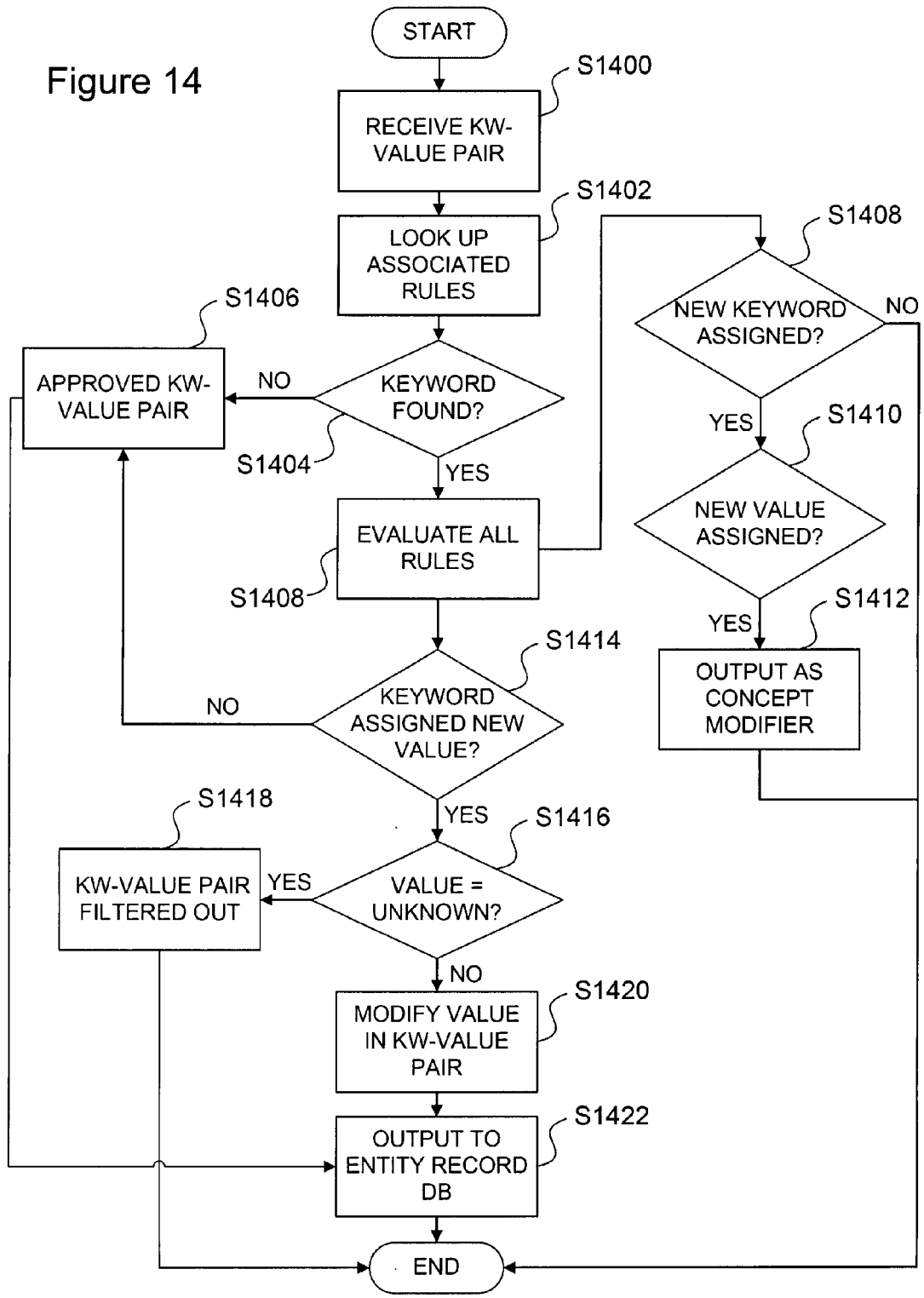
FIG. 14 illustrates another exemplary algorithmic flowchart for a context engine.

Next, FIG. 14 illustrates an exemplary algorithmic flow chart for context engine 202 of FIG. 2. Referring to FIG. 14, a keyword-value pair is received from the truth cases matching unit 308 (S1400). Context engine 202 then queries the context algorithm repository 208 to determine whether the keyword in the keyword-value pair is found on the left-hand side of the stored rules (i.e., whether the keyword satisfies the "if" condition of an "if-then" statement) (S1402). If the keyword is not found (S1404), the keyword-value pair is kept unchanged and is output to the entity record database 110 (S1422). Otherwise, the context engine 202 evaluates the left-hand (i.e., "if") conditions for all the corresponding entity information (e.g., keywords) stored in entity record database 110, including the newly extracted/received keyword-value pair (S1408). If, based on the rules evaluation, the keyword is not assigned a new value (S1414), then the extracted keyword-value pair is approved and output to the entity record database 110. Otherwise, if the keyword does receive a new value and the value is unknown, then the extracted keyword-value pair is filtered out (S1416). In this case, "unknown" means the context engine 202 determined that an error in the value was present and consequently a value of unknown replaces the original value. If, based on the rules evaluation, a new keyword is created and assigned a new value (S1408 and S1410), then the updated keyword-pair is output as a concept modifier in the "truth case" matching runtime phase for re-evaluation by the extraction engine 200 (see, e.g., FIG. 12). The updated keyword-value pair is also output to the entity record database 110. In any case, the keyword-value pairs output to the entity record database 110 may then be used for decision support features.

Decision support features are provided by the decision support unit 112 of FIG. 1. The following sections describe these decision support features in further detail, with reference to FIGS. 15 and 16.

Triggers for Prompting

As discussed previously, triggers are a result of a comparison between the harmonized data elements of the entity record database 110 (i.e., keyword-value pairs and corresponding time stamp information extracted from unstructured and/or structured text input) against the guidelines stored in guidelines database 114. There are various types of triggers that may result in appropriate prompts, based on the nature of the trigger and the role of the user. These trigger types may include:

Does Not Conform to Guidelines/Rules/Protocols: When a set of data elements in the entity record database 110 is evaluated by any of the "truth cases" or expectations in the guidelines database 114 and a deficiency is found, then a trigger is created. For example, decision support unit 112 may determine that a patient's record in entity record database 110 contains a lab result which is outside a normal value range, thereby causing a trigger output.

Time-based: Time-based triggers are the result of evaluating the clinical significance of the passage of time, with respect to the patients' different clinical conditions. This process involves a review of the expectations set in the guidelines for certain procedures, reviews, treatments, or tests and looks to determine whether the data elements in the entity record database 110 comply with expectations. If information that is expected to be entered at a certain interval is missing at one or more of the intervals, a prompt is created. For example, decision support unit 112 may determine that a patient's record stored in entity record database 110 does not contain information indicating an annual test for cholesterol was performed in the previous year, thereby causing a trigger output.

Event-based: An event is defined as any time the entity record database 110 is accessed or updated. These events cause a trigger output, thereby causing contextual analysis system 100 to evaluate any new or modified information using the features of text processing unit 108 and/or decision support unit 112.

Missing: Missing triggers generally indicate points in which expected data is not present. For example, a missing trigger may be output by decision support unit 112 after determining that a text field in an EMR application does not contain any text input (e.g., the "Patient Age" text field is left blank). A missing trigger may also be a subset of either a Time-based or Event-based trigger (e.g., periodic exam results are missing for a defined time period).

Missed Opportunity: The missed opportunity trigger may be a subset of Time-based or Event-based triggers. In this case, decision support unit 112 evaluates data beyond the present context of a particular entry (e.g., an entry at an specialized healthcare provider) and instead compares the data in entity record database 110 to a broader set of guidelines to determine whether other actions can or should be taken at that time. For example, a patient might have an appointment with their provider for a particular issue (e.g., a skin rash), and in addition to that particular treatment, decision support unit 112 may determine, based on a comparison with guidelines stored in guidelines database 114, that it is time for an annual EKG and that the EKG could be performed in the same visit. This process may also be applied when an appointment is being scheduled.

Contraindication: Contraindication may be both a trigger and a prompt status. When an event and/or keyword-value pair is registered or if a plan (e.g., an order created for labs or a prescription is requested) is created and stored in the entity record database 110 that could have a negative outcome according to a guideline comparison, a trigger and/or a prompt is generated which must be addressed before further processing may be performed. Contextual analysis system 100 may allow for an override to be performed based on the user's role, but the contraindication prompt should at least be acknowledged.

Prompting Process

Figure 15A:
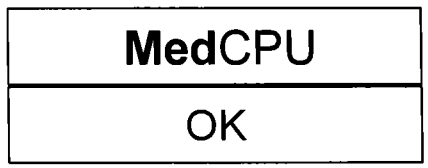

A prompt is an output of the decision support process and specifically, the result of a trigger generation. Prompts may be generated in various levels of severity based on the outcome of the evaluation of the data elements in the entity record database 110 by the guidelines in guidelines database 114. Exemplary stages of prompting based on severity are described below:

Level 0: The first level of prompt may indicate that an entity record in entity record database 110 has been evaluated against guidelines stored in guidelines database 114, wherein the evaluation resulted no trigger generations. This prompting level may, e.g., be indicated by displaying the word "OK" with a green background on an interface for the foundation application 102 or on user interface 116. An exemplary Level 0 prompt is shown in FIG. 15A.

Figure 15B:

Levels 1 and 2: These prompts may indicate that the decision support unit 112 identified some areas of concern that should be addressed, but that they are non-critical in nature. Level 1 is the first to appear. If the user responds to this prompt by acknowledging the prompt or by turning it off, Level 2 will appear at a later stage, based on the significance of this concern, if such area of concern that generated Level 1 prompt remains a concern. These prompting levels may, e.g., be indicated to the user by displaying the word "Important" with a yellow background on an interface for the foundation application 102 or on user interface 116. An exemplary Level 1/2 prompt is shown in FIG. 15B.

Figure 15C:
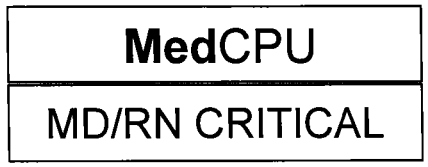

Levels 3 and 4: These prompt levels may indicate that the decision support unit 112 identified some areas of concern that are of a more critical nature and should be addressed quickly. Level 3 is the first to appear. If the user responds to this prompt by acknowledging the prompt or by turning it off, a Level 4 prompt will appear at a later stage, based on the significance of this concern, if such area of concern that generated Level 3 prompt remains a concern. These prompting levels may, e.g., be indicated to the user by displaying the word "Critical" with a red background on an interface for the foundation application 102 or on user interface 116. An exemplary level 3/4 prompt is shown in FIG. 15C.

Figure 15D:
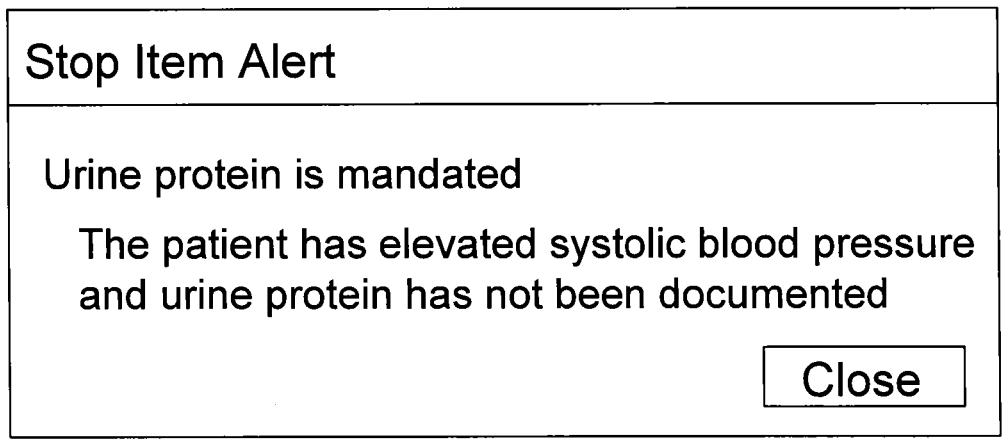

Level 5: This level is indicated to the user by interrupting their work in the foundation application 102, e.g., as an alert box titled "Stop Item Alert". This prompt indicates that critical error was found when evaluating the entity record against the guidelines. This prompt may represent either a particular condition exists or that critical information is missing. In order to proceed from this level of prompt, the user may either make additional entries into the entity record (after which that input will be looped back through the entire extraction and contextual analysis processes) and if the entries satisfy the conditions in decision support unit 112, the alert level will be changed accordingly. Alternatively, the user can make an acknowledgement that they have seen this level of alert and that they are logging themselves as authorized and actively deciding to proceed without addressing this alert. An exemplary Level 5 prompt is shown in FIG. 15D.

Contraindication: This level in indicated to the user by interrupting their work in the foundation application 102, e.g., as an alert box titled "Contraindication"). This prompt indicates that there is something critically wrong that could have a significant deleterious effect when evaluating the entity record against the guidelines. In order to proceed from this level of prompt, the user must either make changes to the entity record (after which that input will be looped back through the entire extraction and contextual analysis processes) and if the entries satisfy the conditions in decision support unit 112, the alert level will be changed accordingly. Alternatively, the user can make an acknowledgement that they have seen this level of alert and that they are logging themselves as authorized and actively deciding to proceed without addressing this alert. An exemplary Contraindication prompt is shown in FIG. 15E.

Level 5+x: Additional levels of criticality can be added as needed for escalation, depending on the nature of the guidelines and the processes they support.

Roles for Prompting

The prompts described above can also be presented to users according to the user's assigned role and/or level of responsibility. See, e.g., roles "MD" and "MD/RN" respectively shown in the FIGS. 15B and 15C prompts. The roles can be tied to roles in the foundation application 102 or can be assigned directly via contextual analysis system 100. Roles may also be aligned across multiple devices/systems (e.g., roles assigned in foundation application 102 may be determined and aligned with contextual analysis system 100). Roles can be assigned based upon varying levels of responsibility, as described in the exemplary properties below:

Responsible/Accountable: This is the highest level of responsibility for this exemplary process and should be assigned to a user with the authority and knowledge of the processes involved such that any prompts based on the triggers can be evaluated and an authoritative determination be made to either alter the activities to satisfy the prompts or to disregard them. In the exemplary case of healthcare, this role may be assigned as, e.g., Medical Doctor (MD). In this case, the doctor is responsible for the evaluation of the clinical information available for the patient (e.g., entity records from entity record database 110), and for acting according to professional and institutional protocols. Contextual analysis system 100 and, in particular, decision support unit 112 provide systematic decision support for these responsibilities, but it is ultimately the user (i.e., the MD) who is responsible for the processes and actions undertaken by the system.

Responsible: This is the second highest level of authority in this exemplary process and should be assigned to a user who is trained and capable of undertaking most, if not all, activities required. There may be a subset of processes or alerts that this user may not be authorized or trained to undertake. In the exemplary case of healthcare, this role may be assigned as, e.g., Registered Nurse (RN).

Central Monitor: This role is not representative of an individual user, but more of an institutional check that is used to present to the different users with more advanced prompt levels. Access to this role may also be based on the user role and both Responsible/Accountable and Responsible users (e.g., MDs and RNs) may have this access. The function of this exemplary role is that it protects against negative outcomes resultant from unaddressed prompts. For example, a Central Monitor function may be included in contextual analysis system 100 that allows for an actual physical mapping of the area of work (e.g., a floor of a hospital). Any entities (e.g., patient records in entity record database 110) that have a configured level of alert associated with them will alert the Central Monitor requesting attention.

In addition to the above exemplary roles, escalation conditions can be configured in contextual analysis system 100 to enact a Chain of Command feature that escalates prompt alerts from to more senior roles if configured conditions are not met.

Looping in Decision Support

Any event that occurs on the foundation application 102 triggers an evaluation of the corresponding entity record in entity record database 110 against the applicable guidelines stored in guidelines database 114. A similar trigger may occur when a user responds to any triggers, resulting in recursive looping in contextual analysis system 100. This looping process may occur in real-time as the user interacts with the application. Moreover, the structuring and tagging of data in the guidelines database 114 and the entity record database 110 allow for this looping process to occur in sub-second timeframes, virtually undetectable by the user.

Figure 16:
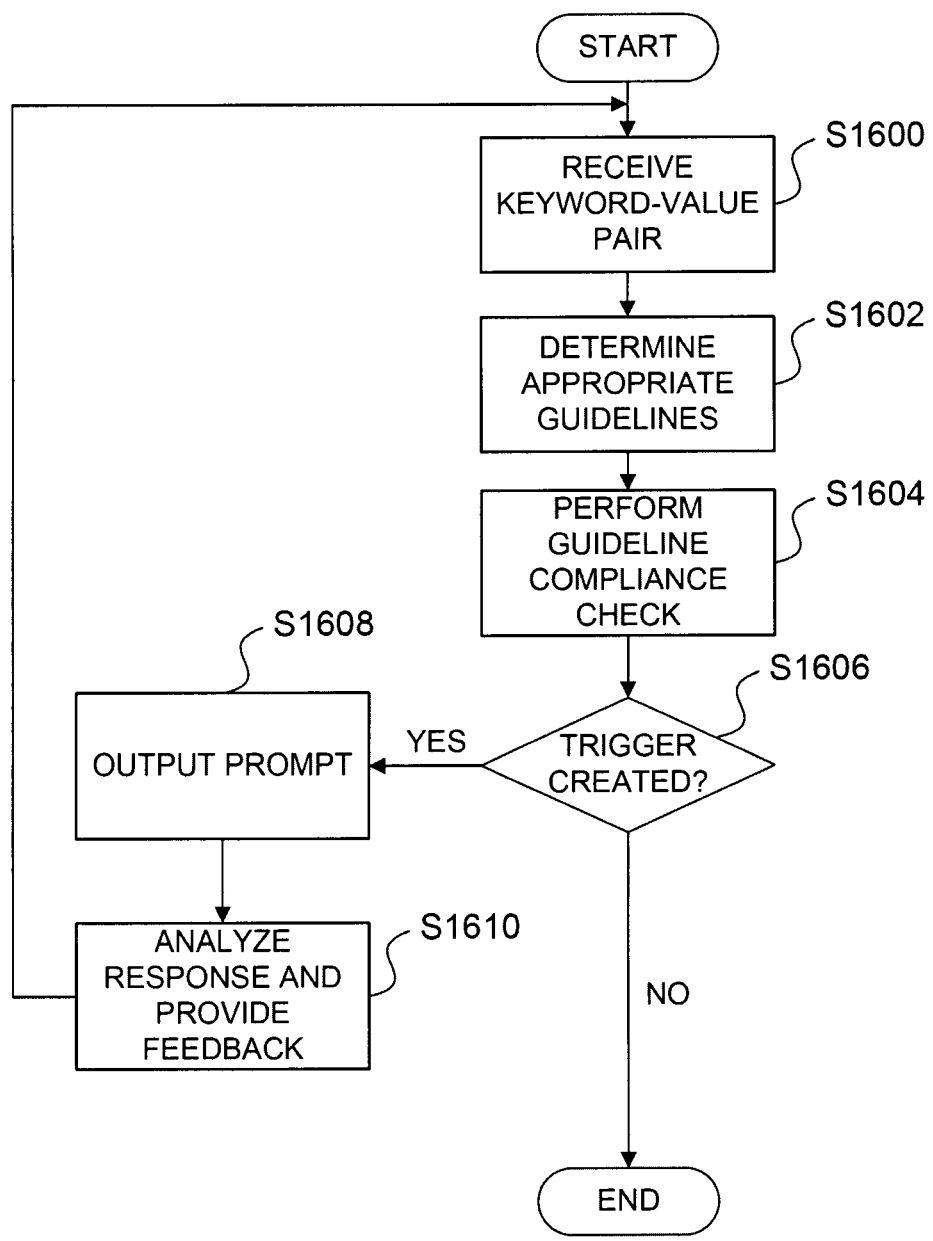
FIG. 16 illustrates an exemplary algorithmic flowchart for a decision support unit.

FIG. 16 is an exemplary algorithmic flowchart illustrating the above-described features of decision support unit 112. As shown in FIG. 16, decision support unit 112 first receives a keyword-value pair for an entity (e.g., a patient) from entity record database 110 (S1600). Next, decision support unit 112 determines the appropriate guidelines with which to evaluate the input data (S1602). The appropriate guidelines are then retrieved from guidelines database 114 and a guidelines compliance check is performed (S1606). A trigger is then created indicating the guidelines compliance check result. The trigger may be one of the Level 0-5 triggers described above, or may be another trigger type indicating compliance (or lack thereof) with the guidelines. A prompt is then generated based on the generated trigger (S1608). The prompt may be one of the prompts described above with reference to FIGS. 15A-E, or may be another prompt type that provides information or takes a predetermined action. Any response received from the user as a result of the prompt, or any automatic action taken by the system is then analyzed and recursive looping is performed to continually analyze the entity's record for decision support purposes (S1610).

Figure 17:
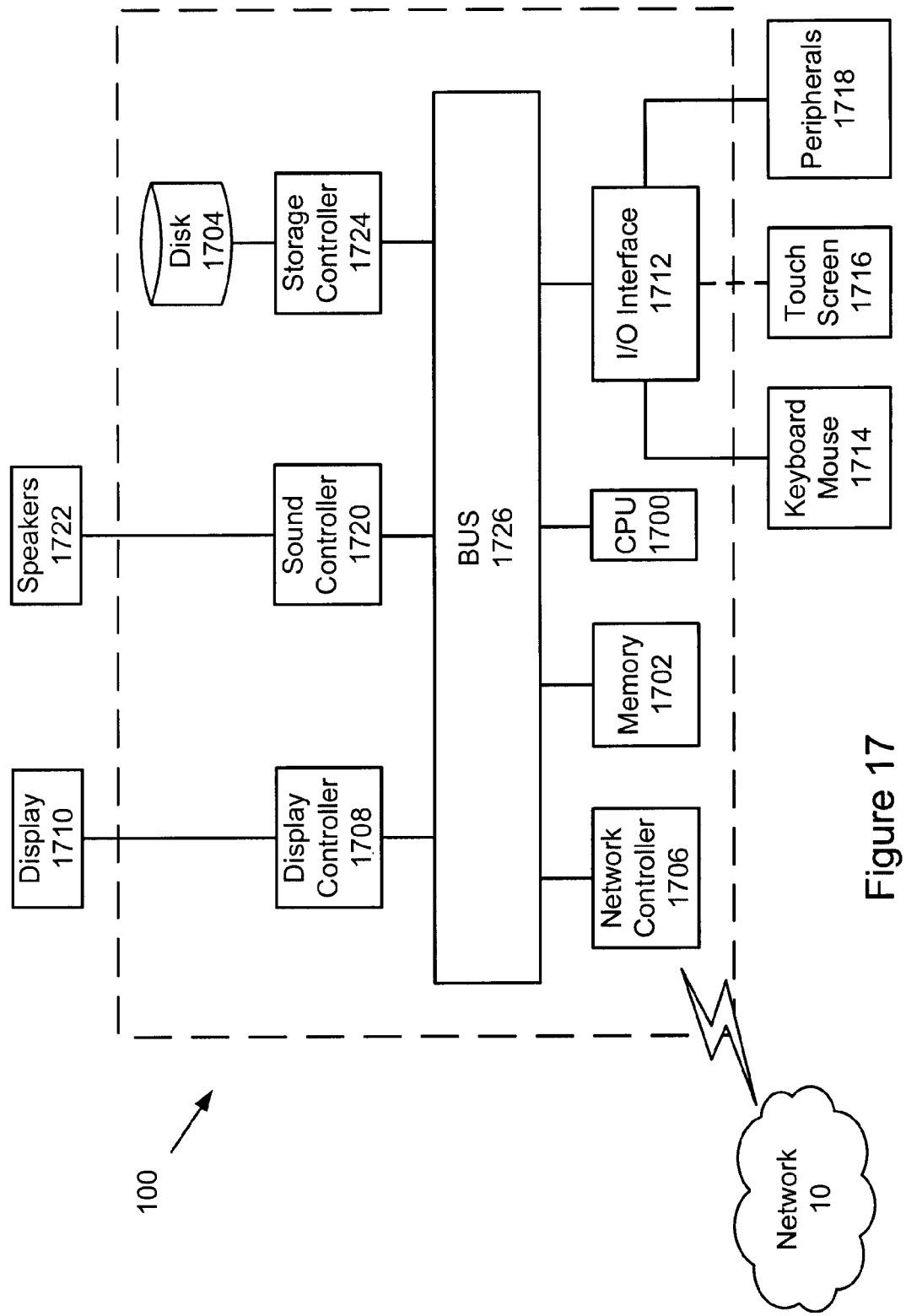
FIG. 17 illustrates a schematic block diagram of a contextual analysis system according to an exemplary hardware embodiment.

Next, a hardware description of the contextual analysis system 100 according to exemplary embodiments is described with reference to FIG. 17. In FIG. 17, the contextual analysis system 100 includes a CPU 1700 which performs the processes described above. The process data and instructions may be stored in memory 1702. These processes and instructions may also be stored on a storage medium disk 1704 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing system with which the contextual analysis system 100 communicates, such as a server or computer.

Further, the claimed advancements may be provided as a utility application, background daemon, or component of an operating system, or combination thereof, executing in conjunction with CPU 1700 and an operating system such as Microsoft Windows 7, UNIX, Solaris, LINUX, Apple MAC-OS and other systems known to those skilled in the art.

CPU 1700 may be a Xenon or Core processor from Intel of America or an Opteron processor from AMD of America, or may be other processor types that would be recognized by one of ordinary skill in the art. Alternatively, the CPU 1700 may be implemented on an FPGA, ASIC, PLD or using discrete logic circuits, as one of ordinary skill in the art would recognize. Further, CPU 1700 may be implemented as multiple processors cooperatively working in parallel to perform the instructions of the inventive processes described above.

The contextual analysis system 100 in FIG. 17 also includes a network controller 1706, such as an Intel Ethernet PRO network interface card from Intel Corporation of America, for interfacing with network 10. As can be appreciated, the network 10 can be a public network, such as the Internet, or a private network such as an LAN or WAN network, or any combination thereof and can also include PSTN or ISDN sub-networks. The network 10 can also be wired, such as an Ethernet network, or can be wireless such as a cellular network including EDGE, 3G and 4G wireless cellular systems. The wireless network can also be WiFi, Bluetooth, or any other wireless form of communication that is known.

The contextual analysis system 100 further includes a display controller 1708, such as a NVIDIA GeForce GTX or Quadro graphics adaptor from NVIDIA Corporation of America for interfacing with display 1710, such as a Hewlett Packard HPL2445w LCD monitor. A general purpose I/O interface 1712 interfaces with a keyboard and/or mouse 1714 as well as a touch screen panel 1716 on or separate from display 1710. General purpose I/O interface 1712 also connects to a variety of peripherals 1718 including printers and scanners, such as an OfficeJet or DeskJet from Hewlett Packard.

A sound controller 1720 is also provided in the contextual analysis system 100, such as Sound Blaster X-Fi Titanium from Creative, to interface with speakers/microphone 1722 thereby providing sounds and/or music. The speakers/microphone 1722 can also be used to accept dictated words as commands for controlling the contextual analysis system 100 or for providing location and/or property information with respect to the target property.

The general purpose storage controller 1724 connects the storage medium disk 1704 with communication bus 1726, which may be an ISA, EISA, VESA, PCI, or similar, for interconnecting all of the components of the contextual analysis system 100. A description of the general features and functionality of the display 1710, keyboard and/or mouse 1714, as well as the display controller 1708, storage controller 1724, network controller 1706, sound controller 1720, and general purpose I/O interface 1712 is omitted herein for brevity as these features are known.

The functions of the exemplary embodiments described herein may also be executed by various distributed components of a system. For example, one or more processors may execute these system functions, wherein the processors are distributed across multiple components communicating in a network. The distributed components may include one or more client and/or server machines, in addition to various human interface and/or communication devices (e.g., display monitors, smart phones, tablets, personal digital assistants (PDAs)). The network may be a private network, such as a LAN or WAN, or may be a public network, such as the Internet. Input to the system may be received via direct user input and/or received remotely either in real-time or as a batch process.

A number of implementations have been described. Nevertheless, it will be understood that various modifications may be made without departing from the spirit and scope of this disclosure. For example, advantageous results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable circuits configured to execute program code and/or computer instructions to execute the functions, processes and algorithms described herein. Additionally, some implementations may be performed on modules or hardware not identical to those described. Accordingly, other implementations are within the scope that may be claimed.

The invention claimed is:

1. A contextual analysis system comprising:
memory;
circuitry comprising at least one data processor that is configured to:
extract data elements from an unstructured text input, the data elements being words or phrases;
identify whether the extracted data elements are relevant to a predetermined context, the predetermined context being a predetermined list of keywords or phrases;
determine, in response to determining that the extracted words or phrases are relevant to the predetermined list of keywords or phrases, whether the extracted words or phrases match an item included in a predetermined list of truth cases, and tagging matched words or phrases as a concept;
tag each concept that is included in a predetermined keyword list as a trigger;
generate a triggered block that includes a sequence of concepts that includes the trigger;
generate a key-word value pair in response to determining that the triggered block matches at least one of the predetermined list of truth cases;
generate a new concept, for inclusion in the triggered block, based on an evaluation of the generated keyword-value pair against an algorithm stored in a context algorithm repository, and based on the information contained in previously generated keyword-value pairs and structured data elements extracted from the same source as the unstructured data elements;
determine whether the new triggered block complies with the predetermined list of truth cases, the predetermined list of truth cases being at least one medical guideline, wherein the at least one medical guideline includes information indicating a periodicity requirement for performing a task in the predetermined context;

determine, based on the relevant data elements, whether the periodicity requirement is violated;

generate a recommendation based on the determination as to whether the information contained in the new triggered block complies with the medical guideline; and output the recommendation to a display interface.

2. The contextual analysis system according to claim 1, wherein the circuitry is configured to:

extract structured data elements that are input from a same source as the unstructured text input; and determine, for both the relevant data elements and the extracted structured data elements, whether the information contained in both sets of data elements complies with the medical guideline.

3. The contextual analysis system according to claim 1, wherein the extraction includes extracting the data elements based on information contained in both the unstructured text input as well as other data sources, which are outside of the unstructured text input and pertain to a same subject matter.

4. The contextual analysis system according to claim 1, wherein the circuitry is configured to determine whether the extracted data elements are relevant based on an evaluation against a contextual algorithm.

5. The contextual analysis system according to claim 1, wherein the circuitry is configured to generate new truth cases for inclusion in the list of truth cases by analyzing the triggered block, identifying a new sequential order of the concepts contained in the triggered block, and generating a new keyword-value pair based on the identification.

6. The contextual analysis system according to claim 1, wherein the circuitry is configured to determine whether the extracted data elements are relevant based on an evaluation of the generated keyword-value pair against an algorithm stored in a context algorithm repository and based on information contained in previously generated keyword-value pairs and structured data elements extracted from a same source as the unstructured data elements.

7. The contextual analysis system according to claim 6, wherein the circuitry is configured to generate new keyword-value pairs based on an evaluation against an algorithm stored in a context algorithm repository, the algorithm using information extracted from previously generated keyword-value pairs and from structured data elements extracted from the same source as the unstructured data elements; and the circuitry is configured to determine whether the extracted data elements are relevant based on a reevaluation of the generated keyword-value pair against the algorithm.

8. The contextual analysis system according to claim 1, wherein the circuitry is configured to discard the generated keyword-value pair if found to be irrelevant based on an evaluation of the generated keyword-value pair against an algorithm stored in a context algorithm repository, and based on information contained in previously generated keyword-value pairs and structured data elements extracted from a same source as the unstructured data elements.

9. The contextual analysis system according to claim 1, wherein the circuitry is configured to change the value of the generated keyword-value pair if found that the value should be changed based on an evaluation of the generated keyword-value pair against an algorithm stored in a context algorithm repository, and based on information contained in previously generated keyword-value pairs and structured data elements extracted from a same source as the unstructured data elements.

10. The contextual analysis system according to claim 1, wherein:

the circuitry is configured to generate a new keyword-value pair based on the generated keyword-value pair; and the new keyword-value pair is generated, by the circuitry, based on an evaluation of the generated keyword-value pair against an algorithm stored in a context algorithm repository, and based on the information contained in the previously generated keyword-value pairs and structured data elements extracted from a same source as the unstructured data elements.

11. The contextual analysis system according to claim 1, wherein:

the medical guideline corresponds to a compliance rule related to the predetermined context; and the compliance rule relates to a time-based requirement or an event-based requirement.

12. The contextual analysis system according to claim 11, wherein the recommendation includes a corrective action to comply with the compliance rule.

13. The contextual analysis system according to claim 1, wherein the circuitry is configured output, to an interface, a prompt indicating whether the information contained in the relevant data elements complies with the medical guideline.

14. The contextual analysis system according to claim 13, wherein when the circuitry determines the information contained in the relevant data elements does not comply with the medical guideline, the recommendation is included in the prompt to provide information as to how to comply with the medical guideline.

15. The contextual analysis system according to claim 1, wherein when the information contained in the relevant data elements indicates the medical guideline is violated, the circuitry outputs a message to an external server, based on the predetermined context.

16. The contextual analysis system according to claim 1, wherein the recommendation is one or more of a treatment recommendation, a course of action recommendation, and a corrective action recommendation.

17. The contextual analysis system according to claim 1, wherein the circuitry is configured to select the medical guideline based on the predetermined context.

18. The contextual analysis system according to claim 1, wherein the predetermined context relates to a patient medical history.

19. The contextual analysis system according to claim 1, wherein the circuitry is further configured to generate a reminder notification based on the determination, and to output the reminder notification to the display interface.

20. A computer implemented method for implementation by one or more data processors forming part of a contextual analysis system, the method comprising:

receiving, by at least one data processor, an unstructured text input on an interface;

extracting, by at least one data processor, data elements from the unstructured text input, the data elements including one or more strings of unstructured text input that include words or phrases;

identifying, by at least one data processor, whether the extracted data elements are relevant to a predetermined context, the predetermined context being a predetermined list of keywords or phrases;

determining, by at least one data processor, in response to determining that the extracted words or phrases are relevant to the predetermined list of keywords or phrases, whether the extracted words or phrases match an item included in a predetermined list of truth cases, and tagging matched words or phrases as a concept;

tagging, by at least one data processor, each concept that is included in a predetermined keyword list as a trigger;

generating, by at least one data processor, a triggered block that includes a sequence of concepts that includes the trigger;

generating, by at least one data processor, a key-word value pair in response to determining that the triggered block matches at least one of the predetermined list of truth cases;

generating, by at least one data processor the circuitry, a keyword-value pair in response to determining that the triggered block matches at least one of the predetermined list of truth cases;

generating, by at least one data processor, a new concept, for inclusion in the triggered block, based on an evaluation of the generated keyword-value pair against an algorithm stored in a context algorithm repository, and based on the information contained in previously generated keyword-value pairs and structured data elements extracted from the same source as the unstructured data elements;

determining by at least one data processor, whether the new triggered block complies with the predetermined list of truth cases, the predetermined list of truth cases being at least one medical guideline, wherein the at least one medical guideline includes information indicating a periodicity requirement for performing a task in the predetermined context;

determining, by at least one data processor based on the relevant data elements, whether the periodicity requirement is violated;

generating, by at least one data processor, a recommendation based on the determining as to whether the information contained in the new triggered block complies with the medical guideline; and outputting, by at least one data processor, the recommendation to a display interface.

21. A non-transitory computer readable medium having instruction stored therein that, when executed by a processor, causes a computer to perform a method of:

receiving an unstructured text input on an interface;

extracting data elements from the unstructured text input based on information contained in both the unstructured text input as well as other sources that are outside of the unstructured text input and pertain to the same subject matter, the data elements being words or phrases;

determining, whether the extracted data elements are relevant to a predetermined context the predetermined context being a predetermined list of keywords or phrases;

determining, in response to determining that the extracted words or phrases are relevant to the predetermined list of keywords or phrases, whether the extracted words or phrases match an item included in a predetermined list of truth cases, and tagging matched words or phrases as a concept;

tagging each concept that is included in a predetermined keyword list as a trigger;

generating a triggered block that includes a sequence of concepts that includes the trigger;

generating a key-word value pair in response to determining that the triggered block matches at least one of the predetermined list of truth cases;

generating a new concept, for inclusion in the triggered block, based on an evaluation of the generated keyword-value pair against an algorithm stored in a context algorithm repository, and based on the information contained in previously generated keyword-value pairs and structured data elements extracted from the same source as the unstructured data elements;

determining whether the new triggered block complies with the predetermined list of truth cases, the predetermined list of truth cases being at lease one medical guideline, wherein the at least one medical guideline includes information indicating a periodicity requirement for performing a task in the predetermined context;

determining, based on the relevant data elements, whether the periodicity requirement is violated;

generating, by the circuitry, a recommendation based on the determination as to whether the information contained in the new triggered block complies with the medical guideline; and outputting the recommendation to a display interface.

* * * * *